(12) United States Patent
Badri et al.

(10) Patent No.: US 10,485,873 B2
(45) Date of Patent: Nov. 26, 2019

(54) MIKTO-ARM STAR POLYMERS FOR DELIVERY OF THERAPEUTIC AGENTS

(71) Applicants: International Business Machines Corporation, Armonk, NY (US); NanoMalaysia Berhad, Kuala Lumpur (MY)

(72) Inventors: Khairiah H. Badri, Bandar Baru Bangi (MY); Emilia B. A. Malek, Selangor (MY); Siti Mariam B. Mohd Nor, Seri Kembangan (MY); Victoria A. Piunova, Los Gatos, CA (US)

(73) Assignees: International Business Machines Corporation, Armonk, NY (US); NanoMalaysia Berhad, Kuala Lumpur (MY)

( * ) Notice: Subject to any disclaimer, the term of this patent is extended or adjusted under 35 U.S.C. 154(b) by 134 days.

(21) Appl. No.: 15/713,971

(22) Filed: Sep. 25, 2017

(65) Prior Publication Data
US 2019/0091338 A1   Mar. 28, 2019

(51) Int. Cl.
| | |
|---|---|
| A61K 47/34 | (2017.01) |
| A61K 47/10 | (2017.01) |
| A61K 47/60 | (2017.01) |
| A61K 31/00 | (2006.01) |
| C08F 293/00 | (2006.01) |

(Continued)

(52) U.S. Cl.
CPC .............. *A61K 47/34* (2013.01); *A61K 8/347* (2013.01); *A61K 8/91* (2013.01); *A61K 31/00* (2013.01); *A61K 47/10* (2013.01); *A61K 47/60* (2017.08); *A61Q 19/00* (2013.01); *C08F 293/00* (2013.01); *A61K 9/00* (2013.01); *A61K 2800/10* (2013.01);

(Continued)

(58) Field of Classification Search
CPC .. A61K 2800/544; A61K 47/34; A61K 47/60; A61K 8/91; A61K 47/10; C08F 293/00
See application file for complete search history.

(56) References Cited

U.S. PATENT DOCUMENTS

| | | | |
|---|---|---|---|
| 8,061,533 B2 | 11/2011 | Mays et al. | |
| 8,765,098 B2 | 7/2014 | Appel et al. | |

(Continued)

FOREIGN PATENT DOCUMENTS

WO    2011163635 A1    12/2011

OTHER PUBLICATIONS

Steinschulte et al. (A nondestructive, statistical method for determination of initiation efficiency: dipentaerythritol-aided synthesis of ternary ABC3 miktoarm stars using a combined "arm-first" and "core-first" approach, Polym. Chem. 2013, 4, 3885-3895).*

(Continued)

*Primary Examiner* — Kortney L. Klinkel
(74) *Attorney, Agent, or Firm* — Michael R. Roberts

(57) ABSTRACT

Mikto-arm star polymers were prepared comprising non-charged hydrophilic poly(ethylene oxide) arms and hydrophobic arms comprising a poly(propylene oxide) chain or phytol group. The polymer arms are covalently linked to a hydrophobic crosslinked polyester core formed by ring opening polymerization of a bis-cyclic ester initiated by mono-nucleophilic polymer arm precursors. The mikto-arm star polymers show improved loading capacity for Coenzyme Q10 (CoQ10).

21 Claims, 2 Drawing Sheets

Coenzyme Q10

(51) Int. Cl.
*A61K 8/34* (2006.01)
*A61Q 19/00* (2006.01)
*A61K 8/91* (2006.01)
*A61K 9/00* (2006.01)
*A61Q 17/00* (2006.01)

(52) U.S. Cl.
CPC ...... *A61K 2800/544* (2013.01); *A61Q 17/005* (2013.01)

(56) References Cited

U.S. PATENT DOCUMENTS

| | | |
|---|---|---|
| 9,399,694 B2 | 7/2016 | Jakubowski et al. |
| 9,597,405 B2 | 3/2017 | Lee et al. |
| 2016/0375143 A1 | 12/2016 | Guanntillake et al. |
| 2017/0081466 A1 | 3/2017 | Kornfield et al. |

OTHER PUBLICATIONS

Aloorkar et al., "Star Polymers: An Overview", In Journal Pharm Sci Nanotech, 2012, vol. 5, pp. 1675-1684; abstract.

Appel et al., "Toward biodegradable nanogel star polymers via organocatalytic ROP", Chem Comm, 2012, pp. 6163-6165.

Bhagath et al., "Star Polymers: An Overview", International Journal of Biological & Pharmaceutical Research. 2013; 4(2): 76-79.

Gao et al., "Arm-First Method as a Simple and General Method for Synthesis of Miktoarm Star Copolymers", JACS, 2007, vol. 129, pp. 11828-11834.

Gao et al., "Low Polydispersity Star Polymers via Cross-Linking Macromonomers by ATRP", JACS, 2006, vol. 128, pp. 15111-15113.

Lapienis, "Star-shaped polymers having PEO arms", Progress in Polymer Science 34 (2009) 852-892.

Matyjaszewski, "Star Copolymers", the Matyjaszewski Polymer Group, Carnegie Mellon University, downloaded from the internet Dec. 13, 2016.

Miller et al., "Water soluble, biodegradable amphiphilic polymeric nanoparticles and the molecular environment of hydrophobic encapsulates: Consistency between simulation and experiment", Polymer 79 (2015), p. 255-261.

Nijenhuis et al., "Crosslinked poly(L-lactide) and poly(e-caprolactone)", Polymer vol. 37, No. 13, 1996, p. 2783-2791.

Ren, et al., "Organic Catalyst-Mediated Ring-Opening Polymerization for the Highly Efficient Synthesis of Polyester-Based Star Polymers", ACS Macro Lett. 2012, 1, 681-686.

Sharma et al., "Design and Evaluation of Multifunctional Nanocarriers for Selective Delivery of Coenzyme Q10 to Mitochondria", Biomacromolecules 2012, 13, 239-252.

Soliman et al., "Dendrimers and miktoarm polymers based multivalent nanocarriers for efficient and targeted drug delivery", Chem. Commun., 2011, 47, 9572-9587.

* cited by examiner

Coenzyme Q10

MIKTO-ARM STAR POLYMERS FOR DELIVERY OF THERAPEUTIC AGENTS

PARTIES TO A JOINT RESEARCH AGREEMENT

This invention was made under a joint research agreement between International Business Machines Corporation and NanoMalaysia Berhad.

BACKGROUND

The invention is related to mikto-arm star polymers for delivery of therapeutic agents, and more specifically to the delivery of hydrophobic drugs and nutraceuticals used in the treatment of a medical condition and/or as dietary supplements.

Nanogel core star polymers (i.e., star polymers having a cross-linked polymer core and polymer arms emanating from, and covalently linked to the core), which have an attractive platform for delivery of drugs and other biologically active cargoes, have been reported (Appel, E. A. et al., "Toward biodegradable nanogel star polymers via organocatalytic ROP", Chemical Communications, 2012, pp. 6163-6165; Miller, R. D. et al., "Water soluble, biodegradable amphiphilic polymeric nanoparticles and the molecular environment of hydrophobic encapsulates: Consistency between simulation and experiment", Polymer, 2015, volume 79, pp. 255-261). Ubiquinone (CoQ10) and its derivatives represent an important class of nutraceuticals, proven to enhance statin and breast cancer therapies. However, the efficacy of CoQ10 is diminished upon direct administration to the patient due to its poor bioavailability. Drug delivery vehicles provide means to overcome this limitation by providing improved solubility and targeted delivery of the cargo. While nanogel-core star polymers present an attractive candidate for CoQ10 delivery, the cargo loading capacity was found to be low, averaging around 3.2 wt % or less based on total weight of the loaded star polymer. A need exists for star polymers having improved loading capacity of hydrophobic cargoes.

SUMMARY

Accordingly, a mikto-arm star polymer is disclosed, comprising:
a crosslinked hydrophobic polymer core C', wherein C' comprises a polymer backbone selected from the group consisting of polyester, polycarbonate, and polyestercarbonate;
a hydrophilic first arm covalently linked to core C', the first arm comprising a poly(ethylene oxide) chain, designated PEG chain; and
a hydrophobic second arm covalently linked to the core, the second arm comprising a poly(propylene oxide) chain, designated PPG chain, or a phytoxy group.

Also disclosed is a composition, comprising:
the mikto-arm star polymer of claim 1;
a therapeutic agent used in a treatment of cellular tissue;
wherein
the therapeutic agent and mikto-arm star polymer are bound by non-covalent interactions.

Further disclosed is a method of a treating a cell, comprising contacting the cell with an aqueous mixture comprising an above-described composition.

Another method is disclosed comprising: i) forming a mixture of the mikto-arm star polymer and a therapeutic agent in a first solvent; and ii) combining the mixture with a second solvent, the second solvent being a non-solvent for the therapeutic agent, thereby forming an above-described composition.

Also disclosed is a mikto-arm star polymer of formula (2).

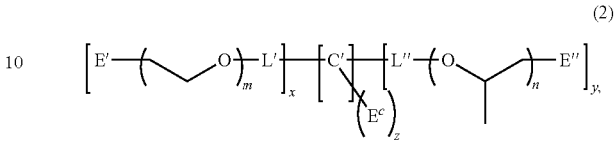

wherein
x is a positive number having a value of 1 or more,
y is a positive number having a value of 1 or more,
z is a positive number having a value of 1 or more,
m is a positive number having an average value of 50 to 600,
n is a positive number having an average value of 10 to 50,
x+y has a value of 6 or more,
C' is a crosslinked polymer core having a valency of x+y+z, and C' comprising a polymer backbone selected from the group consisting of polyester, polycarbonate, and polyestercarbonate,
each $E^c$ is an independent monovalent end group of the core C',
each E' is an independent monovalent end group,
each E" is a independent monovalent end group,
each L' is an independent group selected from the group consisting of single bond and divalent linking groups, and
each L" is an independent group selected from the group consisting of single bond and divalent linking groups.

Further disclosed is mikto-arm star polymer of formula (3):

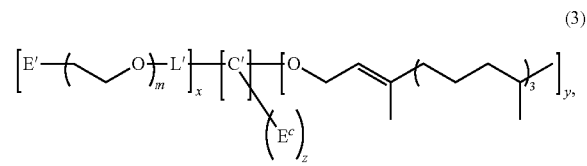

wherein
x is a positive number having a value of 1 or more,
y is a positive number having a value of 1 or more,
z is a positive number having a value of 1 or more,
m is a positive number having an average value of 50 to 600,
x+y has a value of 6 or more,
C' is a crosslinked polymer core having a valency of x+y+z, and C' comprising a polymer backbone selected from the group consisting of polyester, polycarbonate, and polyestercarbonate,
each $E^c$ is an independent monovalent end group of the core C',
each E' is an independent monovalent end group, and
each L' is an independent group selected from the group consisting of single bond and divalent linking groups.

The above-described and other features and advantages of the present invention will be appreciated and understood by

DETAILED DESCRIPTION

Disclosed are unimolecular mikto-arm star polymers comprising a crosslinked polymer core for the delivery and release of hydrophobic therapeutic agents, which include drugs and nutraceuticals used in a treatment of cellular tissue (e.g., treatment of a wound and/or a disease, cosmetic treatment). More specific nutraceuticals include ubiquinone (Coenzyme-Q10, also referred to herein as CoQ10) and its reduced form ubiquinol. Herein, the term "mikto-arm star polymer" is a star polymer macromolecule having at least two polymer arms of different chemical structure. The polymer arms are bound covalently to crosslinked polymer core. The term "nutraceutical" means a nutrient (e.g., vitamins, dietary supplements including CoQ10) used in the prevention or treatment of a disease. Also disclosed are compositions referred to as loaded mikto-arm star-polymers that comprise a mikto-arm star polymer macromolecule and a biologically active material (cargo), which are bound by non-covalent interactions. The mikto-arm star polymers can have significantly higher loading capacities compared to amphiphilic star polymers comprising polymer arms of identical chemical structure. The loaded mikto-arm star polymers are water-dispersible nano-sized particles having an average diameter of about 20 nm to about 200 nm. The loaded mikto-arm star polymers have potential utility in treatments of medical conditions that include delivery and release of a hydrophobic cargo. The loaded mikto-arm star polymers also have utility in disease prevention (e.g., as dietary supplements).

The mikto-arm star polymers are preferably biodegradable and/or biocompatible. The term "biodegradable" is defined by the American Society for Testing and Materials as degradation caused by biological activity, especially by enzymatic action, leading to a significant change in the chemical structure of the material. For purposes herein, a material is biodegradable if it undergoes 60% biodegradation within 180 days in accordance with ASTM D6400.

Figure 1:
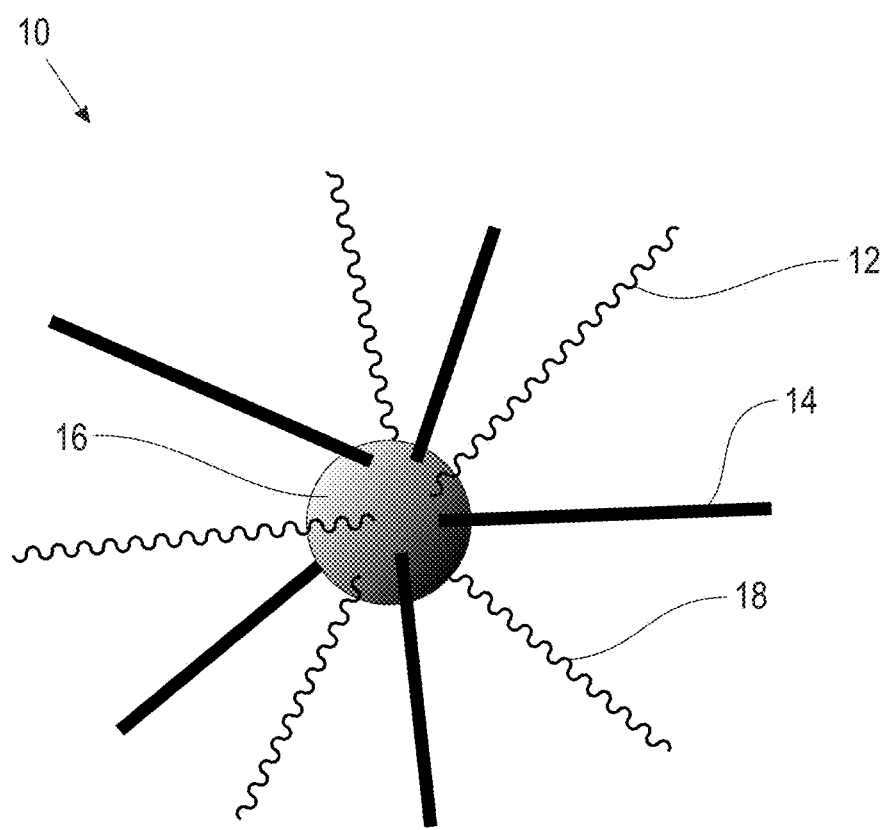
FIG. 1 is a 3-dimensional molecular model of an amphiphilic mikto-arm star polymer having a hydrophilic polymer arms and a hydrophobic polymer arms.

FIG. 1 is a drawing of a 3-dimensional representation of an exemplary mikto-arm star polymer macromolecule. Mikto-arm star polymer 10 comprises 3 or more independent non-charged hydrophilic polymer arms 12 comprising a poly(ethylene oxide) chain (PEG chain) and 3 or more independent hydrophobic polymer arms 14. Hydrophobic polymer arms 14 can comprise a poly(propylene oxide) chain (PPO chain) or a phytoxy group. Each of polymer arms 12 and 14 is covalently linked to a central crosslinked nanogel core 16 by a single bond or a divalent linking group (e.g., a terminal ethylene oxide group (*—CH$_2$CH$_2$O—*) of the PEG chain or a terminal propylene oxide group (*—CH$_2$CH(CH$_3$)O—*) of a PPG chain). Interstitial region 18 between the polymer arms is also indicated. The core 16 is preferably hydrophobic. Core 16 can be a living core (i.e., having end groups capable of initiating a polymerization) or a core whose end groups are capable of undergoing another chemical modification. Preferably, core 16 is a crosslinked polyester, polycarbonate, or polyestercarbonate network formed by ring opening polymerization of a monomer selected from the group consisting of bis-cyclic esters, bis-cyclic carbonates, or a combination thereof, respectively. Herein, a polyestercarbonate is a polymer whose backbone comprises ester and carbonate repeat units linked in a chain.

The mikto-arm star polymer macromolecule can comprise two or more sets of chemically distinct arms. In an embodiment, the mikto-arm star polymer macromolecule comprises two sets of chemically distinct arms and has a structure in accordance with formula (1):

wherein x is a positive number having a value of 1 or more, y is a positive number having a value of 1 or more, z is a positive number having a value of 1 or more, x+y has a value of 6 or more, C' is a crosslinked polymer core having a valency of x+y+z, each A' is an independent first polymer arm comprising a poly(ethylene oxide) chain, each B' is an independent second polymer arm comprising a poly(propylene oxide) chain or a phytoxy group, and each E' is an independent end group of C'.

Variable x represents the average number of arms A'. Variable y represents the average number of arms B'. Variable z represents the average number of end groups of C'.

The term x+y means the sum of x plus y. The term x+y+z means the sum of x plus y plus z. This notation applies to any other sums expressed below.

Preferably, polymer arms A' and B' are linear, whereas the core C' is a branched and crosslinked polymer network, referred to as a nanogel core. Herein, a "linear" polymer chain has one polymer backbone connecting two polymer chain ends, as opposed to a branched polymer having two or more intersecting polymer backbones and three or more polymer chain ends. Herein, a polymer backbone is the collection of atomic centers providing the shortest path of covalent bonds from one polymer chain end to an opposing polymer chain end. The polymer backbone can include atomic centers of one or more polymer chain portions joined by respective linking groups. A given polymer chain portion can be a homopolymer, random copolymer, or block copolymer chain of the repeat units thereof. The atomic centers of the linear polymer backbone can include one or more atomic centers of any linking groups joining the polymer chain portions. The polymer arms are linear portions of the mikto-arm star polymer macromolecule. The core is a non-linear portion of the mikto-arm star polymer macromolecule due to its branched structure. The star polymer macromolecule as a whole is therefore a non-linear polymer structure.

More specific mikto-arm star polymers have structures according to formula (2).

$$\left[E'-\left(\diagup\diagup O\right)_m-L'\right]_x-\left[C'\left(-L''-(O\diagdown\diagdown)_n-E''\right)_y\left(E^c\right)_z\right]$$ (2)

wherein
- x is a positive number having a value of 1 or more,
- y is a positive number having a value of 1 or more,
- z is a positive number having a value of 1 or more,
- m is a positive number having an average value of 50 to 600,
- n is a positive number having an average value of 10 to 50,
- x+y has a value of 6 or more,
- C' is a crosslinked polymer core having a valency of x+y+z,
- each $E^c$ is an independent monovalent end group of the core C',
- each E' is an independent monovalent end group,
- each E" is a independent monovalent end group,
- each L' is an independent group selected from the group consisting of single bond and divalent linking groups, and
- each L" is an independent group selected from the group consisting of single bond and divalent linking groups.

E' and E" can be any suitable end groups. Non-limiting exemplary E' and E" groups include $C_1$-$C_{20}$ alkyl and aryl oxy groups ($R^eO$—*), $C_1$-$C_{20}$ alkyl and aryl carboxy groups ($R^eC(=O)O$—*), and $C_1$-$C_{20}$ alkyl and aryl carboxamido groups ($R^eC(=O)N(H)$—*), wherein $R^e$ is a monovalent hydrocarbon radical. More specific E' and E' groups include methoxy, ethoxy, propoxy, n-butoxy, tert-butoxy, acetoxy, and phenoxy groups. In an embodiment E' is methoxy. In another embodiment E" is n-butoxy.

$E^c$ can be any suitable end group (e.g., hydrogen, acetoxy). In an embodiment, $E^c$ is hydrogen.

In an embodiment, m has an average value of 80 to 200. In another embodiment, n has an average value of 10 to 30.

L' can be any suitable divalent linking group with the proviso that the drug loading and drug release properties of the star polymers are not adversely affected. In an embodiment, L' is a single bond.

L" can be any suitable linking group with the proviso that the drug loading and drug release properties of the star polymers are not adversely affected. In an embodiment, L" is a single bond.

Other more specific mikto-arm star polymers have structures according to formula (3).

$$\left[E'-\left(\diagup\diagup O\right)_m-L'\right]_x-\left[C'\left(-\overbrace{O\diagdown\diagdown\diagdown\diagdown}^{\text{Phytoxy group}}\right)_y\left(E^c\right)_z\right]$$ (3)

wherein
- x is a positive number having a value of 1 or more,
- y is a positive number having a value of 1 or more,
- z is a positive number having a value of 1 or more,
- m is a positive number having an average value of 50 to 600,
- x+y has a value of 6 or more,
- C' is a crosslinked polymer core having a valency of x+y+z,
- each $E^c$ is an independent monovalent end group of the core C',
- each E' is an independent monovalent end group, and
- each L' is an independent group selected from the group consisting of single bond and divalent linking groups.

In the above structure, the hydrophobic polymer arms are phytoxy groups. C', $E^c$, E', and L' can have the meanings described further above.

Ring Opening Polymerization (ROP)

The star polymer can be prepared in one reaction vessel by organocatalyzed ROP using pre-formed polymer arm precursors comprising nucleophilic end groups capable of initiating the ROP (e.g., alcohol groups). The ROP forms the core C'. The core C' can be a homopolymer, random copolymer, or block copolymer network.

The ROP reaction mixture comprises two or more chemically distinct polymeric ROP initiators (precursor arms of the mikto-arm star polymer), a solvent, an organocatalyst, an optional accelerator, and a multi-functional cyclic carbonyl monomer. One of the ROP initiators comprises a poly(ethylene oxide) chain and is referred to as a "PEG initiator." A second ROP initiator is a material selected from the group consisting of i) polymers comprising a poly(propylene oxide) chain ("PPG initiator" after poly(propylene glycol), ii) phytol, and iii) combinations thereof. Phytol has the structure:

$$HO\diagup\diagdown=\diagup(\diagdown\diagup)_3$$

Phytol can be used as a single isomer or as a mixture of isomers.

The multi-functional cyclic carbonyl monomer is selected from the group consisting of multi-functional cyclic ester monomers, multi-functional cyclic carbonate monomers, and combinations thereof.

Optionally, the ROP reaction mixture can comprise a diluent cyclic carbonyl monomer selected from the group consisting of cyclic ester monomers, cyclic carbonate monomers, and combinations thereof.

Agitating the reaction mixture at a temperature of 15° C. to 150° C. effects ring opening polymerization of the multi-functional cyclic carbonyl monomer(s), thereby forming a mikto-arm star polymer. This initial ROP effectively links 6 or more precursor arms to a single globular crosslinked polymer core network. After the initial ROP, the crosslinked polymer core can have an aliphatic polyester backbone, an aliphatic polycarbonate backbone, or an aliphatic polyester-carbonate backbone. The initial ROP produces a living core comprising alcohol end groups capable of initiating another ROP. The core can be extended using one or more sequential ROPs employing the same or different cyclic carbonyl monomer(s) for each ROP.

The optional mono-functional cyclic carbonyl monomers can serve to adjust crosslink density, hydrophobicity, and swelling properties of the core in a given solvent.

Scheme 1 illustrates the preparation of a mikto-arm star polymer by a one-step ring opening polymerization (Examples 1-5 further below). The ROP polymeric initiators MPEG-OH and BPPG-OH (precursor arms) are commercially available polymers.

variable q represents the degree of polymerization (DP) of the core. The variable z indicates the number of core-terminating alcohol groups. The core-terminating alcohol groups can initiate another ROP if desired.

The mikto-arm star polymers typically have a total of 20 to 40 polymer arms (i.e., x+y=20 to 40).

For simplicity, all examples herein assume the ideal case that all initiating groups react and, therefore, the length of

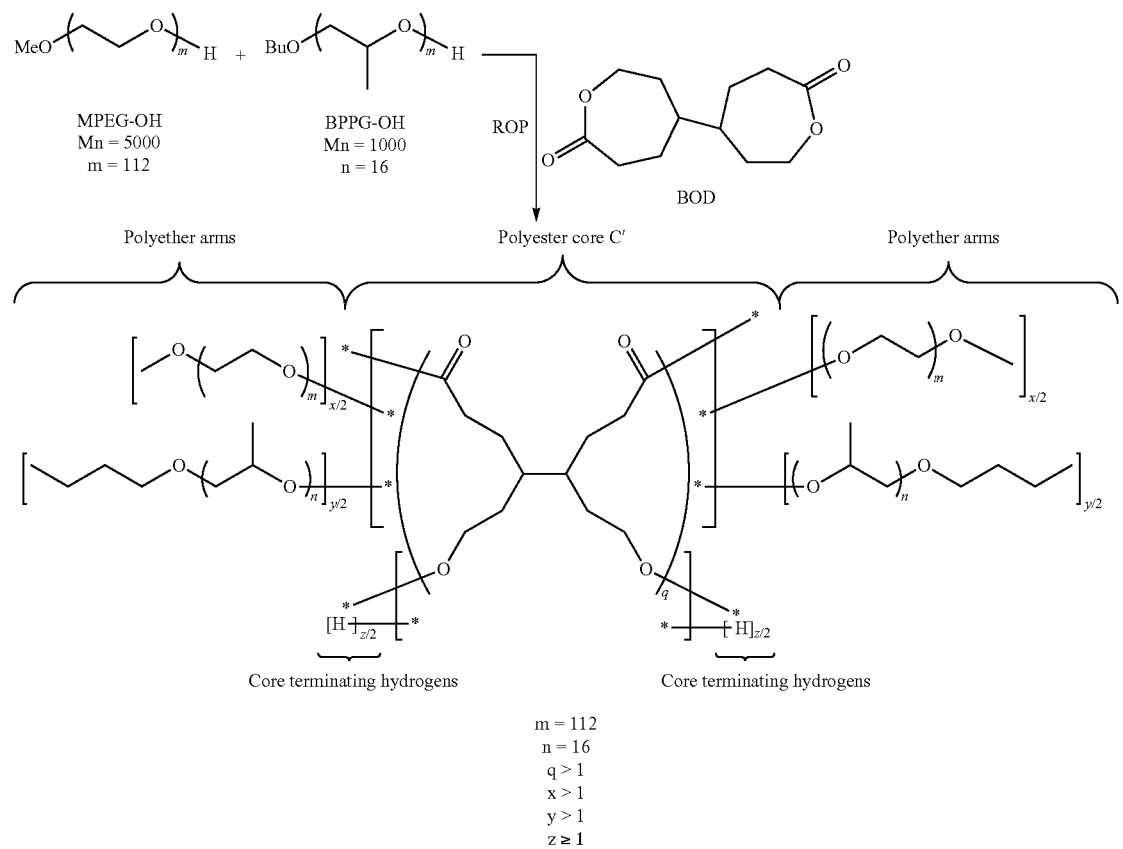

Herein, an atomic center shown linked to an asterisk (*——) indicates the atomic center is covalently linked to another unspecified atomic center of a chemical structure represented by the asterisk. The square brackets in the above structures enclose polymer chains. For this example, it should be understood that a given carbonyl group of the core can be linked to an oxygen end group of a polyether arm or to an ester oxygen of another ring opened BOD unit of the core. A given divalent ester oxygen of the core can be linked to a core-terminating hydrogen or a carbonyl group of the core. A given polyether arm can be linked to a carbonyl group of the core. A given hydrogen end group of the core can be linked to an alkoxy group (R—O—*) of the core. The variable x represents the number of methoxy terminated poly(ethylene oxide) arms (referred to as MPEG arms). The variable y represents the number of n-butoxy terminated poly(propylene oxide) arms (referred to as BPPG arms). The polymer chains may be described by the division of the number of moles of monomer units by the number of moles of initiating sites. However, the reaction of 100% of the initiating sites is not a requirement for successful implementation of the invention. Non-reacted nucleophilic initiating groups can serve as additional reaction or initiator sites during subsequent synthetic processes. Therefore, it is advantageous that a high percentage of the nucleophilic initiating groups undergo the ring opening reaction.

The star polymers and any component used to prepare the star polymers can be stereospecific or non-stereospecific. As examples, a stereospecific monomer and/or stereospecific repeat unit i) has a non-superposable mirror image and ii) comprises one or more asymmetric tetravalent carbons (i.e., tetrahedral $sp^3$ carbons). Each asymmetric tetravalent carbon is assigned an R or S symmetry based on Cahn-Ingold-Prelog (CIP) symmetry rules. If, for example, a stereospecific repeat unit has one asymmetric tetravalent carbon, then the stereospecific repeat unit can be present substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present substantially as the R,R stereoisomer, substantially as the R,S stereoisomer, substantially as the S,S stereoisomer, or substantially as the S,R stereoisomer.

More specific details of the ROP reaction components and conditions are provided in the following sections.

Multi-Functional Cyclic Carbonyl Monomers

Multi-functional cyclic carbonyl monomers comprise two or more cyclic carbonyl groups capable of ring-opening polymerization. More specific multi-functional cyclic carbonyl monomers include bis-cyclic ester monomers and bis-cyclic carbonate monomers. The multi-functional cyclic carbonyl monomers can be used singularly or in combination.

More specific non-limiting examples of bis-cyclic ester monomers include the following compounds.

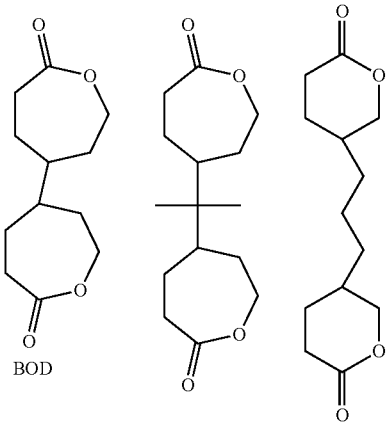

BOD

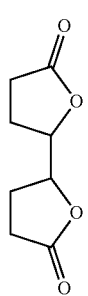

More specific non-limiting bis-cyclic carbonate monomers include the following.

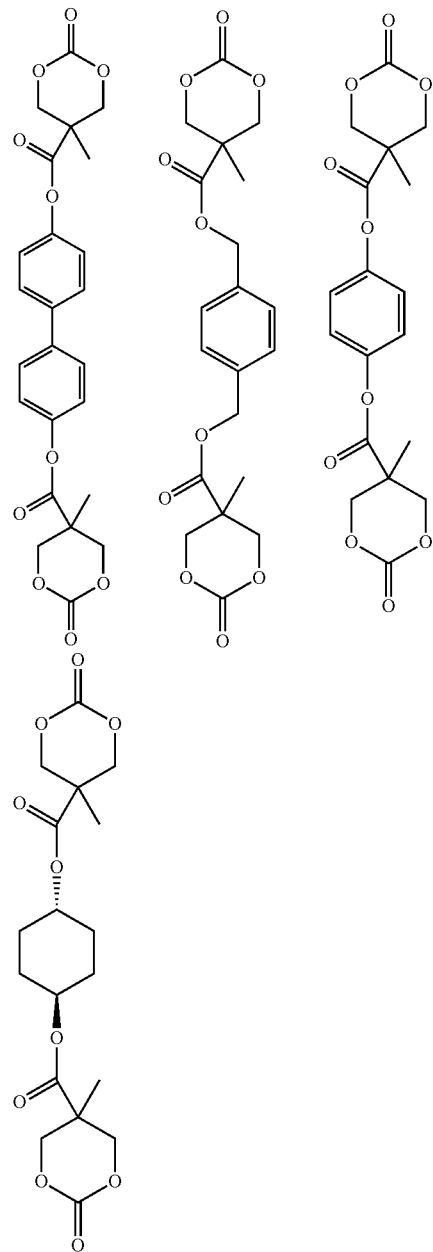

Non-limiting examples of tris-cyclic carbonate monomers include the following.

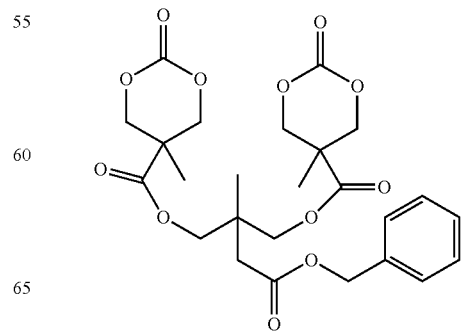

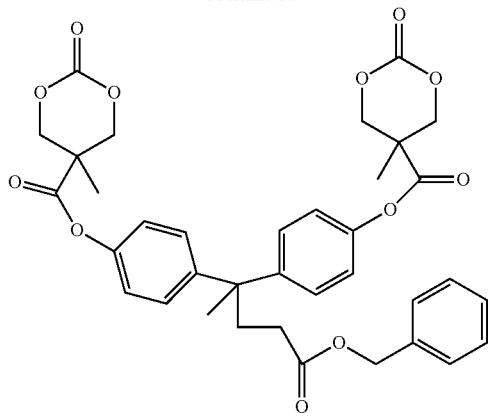

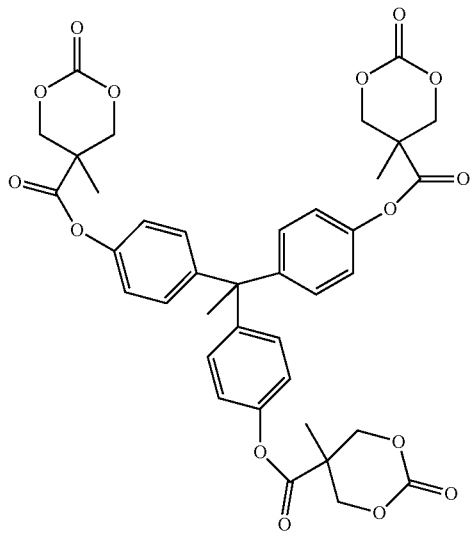

Diluent Cyclic Carbonyl Monomers

Diluent cyclic carbonyl monomers include mono-functional cyclic ester monomers and mono-functional cyclic carbonate monomers. The diluent cyclic carbonyl monomers can be used singularly or in combination.

More specific examples of diluent cyclic ester monomers include the following.

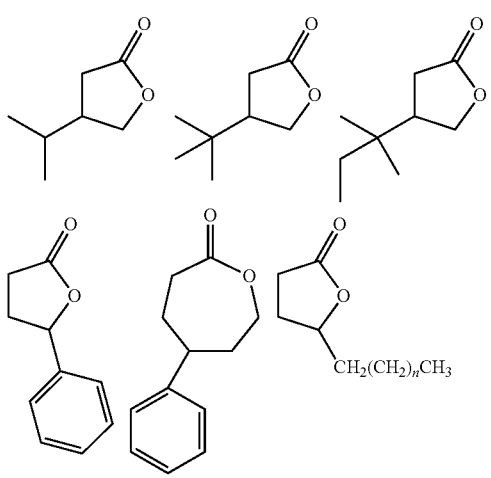

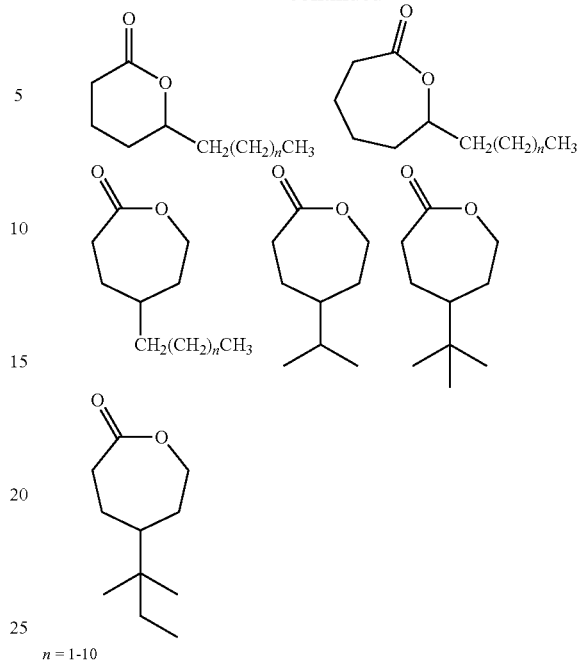

$n = 1\text{-}10$

Other diluent cyclic ester monomers have a structure according to formula (4):

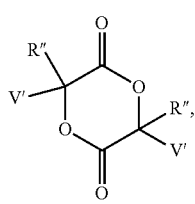

(4)

wherein

V is a monovalent $C_3$-$C_{50}$ hydrocarbon radical, and

R" is a monovalent radical selected from the group consisting of hydrogen and alkyl groups comprising 1 to 6 carbons.

Non-limiting examples of cyclic ester monomers of formula (4) include those listed below.

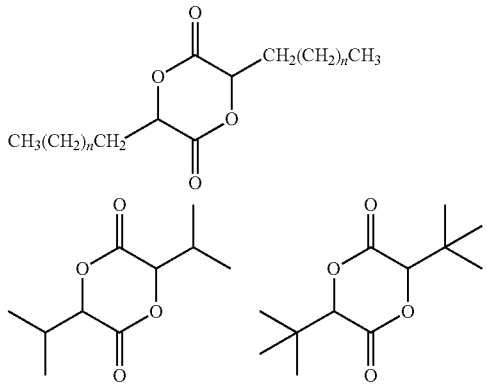

-continued

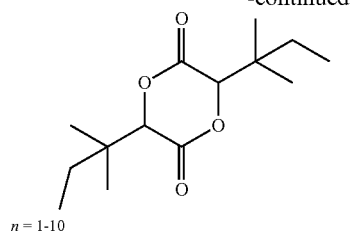

n = 1-10

Still other diluent cyclic ester monomers include those listed below.

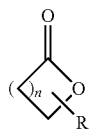

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH$_3$; n = 1: beta-Butyrolactone (b-BL)
R = CH$_3$; n = 2: gamma-Valerolactone (g-VL)

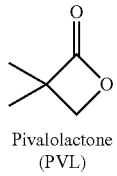

Pivalolactone (PVL)

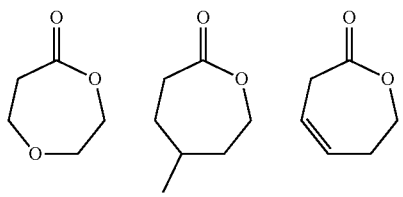

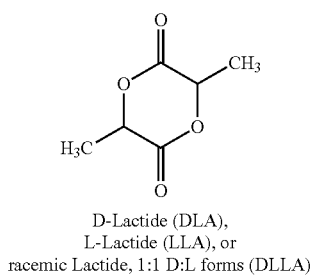

D-Lactide (DLA),
L-Lactide (LLA), or
racemic Lactide, 1:1 D:L forms (DLLA)

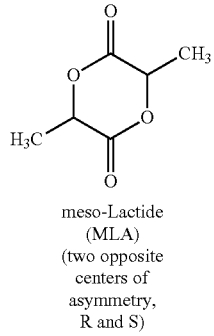

meso-Lactide (MLA)
(two opposite centers of asymmetry, R and S)

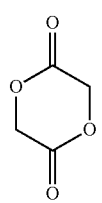

Glycolide (GLY)

Non-limiting examples of diluent cyclic carbonate monomers include the following.

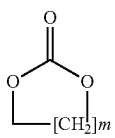

m = 1, Trimethylene carbonate (TMC)
m = 2, Tetramethylene carbonate (TEMC)
m = 3, Pentamethylene carbonate (PMC)

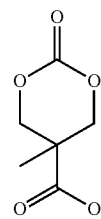

R = hydrogen (MTCOH)
R = methyl (MTCOMe)
R = t-butyl (MTCO$^t$Bu)
R = ethyl (MTCOEt)

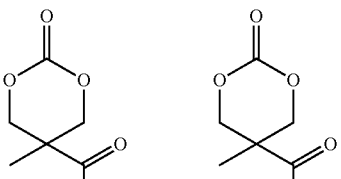

(MTCOBn)

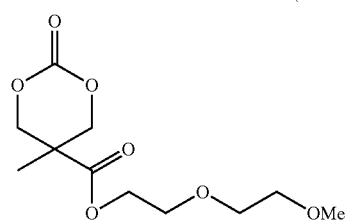

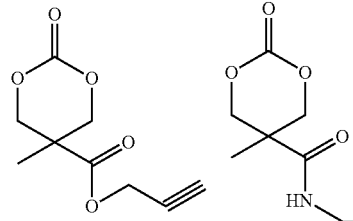

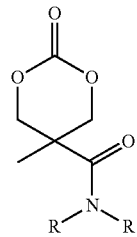

R = methyl
R = iso-propyl

PEG Initiator

The initial ROP reaction mixture comprises a PEG initiator. The PEG initiator has one nucleophilic end group selected from the group consisting of alcohols, amines, and thiols. The initiator can have a number average molecular weight (Mn) of about 1000 to about 10000, preferably 1000 to about 5000.

The PEG initiator has a structure according to formula (I-1):

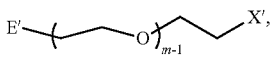
(I-1)

wherein
m has an average value of about 50 to about 600,
E' is a monovalent end group,
X' is a nucleophilic monovalent group selected from the group consisting of *—OH, *—NH$_2$, and *—SH, which is capable of initiating a ROP.

E' has the same meaning discussed further above. In an embodiment, m' has an average value of about 100 to about 200, E' is methoxy, and X' is *—OH (i.e., the PEG initiator is mono-methyl end-capped poly(ethylene glycol) (MPEG-OH)).

PPG Initiator

When present, the PPG initiator has one nucleophilic end group selected from the group consisting of alcohols, amines, and thiols. The initiator can have a number average molecular weight (Mn) of about 100 to about 2000, preferably 500 to about 1500.

Preferably, the PPG initiator for the ROP has a structure according to formula (I-2):

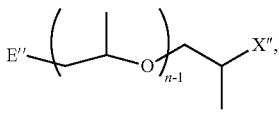
(I-2)

wherein
n has an average value of about 10 to about 50,
E" is a monovalent end group,
X" is a nucleophilic monovalent group selected from the group consisting of *—OH, *—NH$_2$, and *—SH, which is capable of initiating a ROP.

E" has the same meaning discussed further above. In an embodiment, n has an average value of about 10 to about 30, E" is n-butoxy, and X" is *—OH (i.e., the PPG initiator is mono-butyl end-capped poly(propylene glycol) (BPPG-OH)).

The hydrophilic PEG initiator and the hydrophobic PPG initiator can be used in a PEG initiator:PPG initiator molar ratio of between 100:0 and 50:50, where a mole of PEG initiator and PPG initiator is based on number average molecular weight (Mn) of the polymer.

Likewise, the hydrophilic PEG initiator and hydrophobic phytol initiator can be used in a PEG initiator:Phytol molar ratio of between 100:0 and 50:50.

ROP Catalysts

The ROP reaction mixture preferably includes an organocatalyst whose chemical structure contains none of the following restricted metals. An organocatalyst overcomes the problem of entrapped metal, in addition to providing a platform for synthesizing ring opened polymers of controlled, predictable molecular weights and narrow polydispersities.

The term "restricted metals" includes ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Preferably, the star polymer formed by the ROP also contains no detectable amount of the above restricted metals. Structural metal from a polymerization catalyst can be entrapped by the crosslinked core. The trapped metal can be cytotoxic and can interfere with the binding, release and/or the function of a cargo material. Therefore, star polymers comprising a minimum of each restricted metal are highly desirable.

No restriction is placed on the concentration of boron, silicon, or any individual alkali metal, with the proviso that the star polymer has desirable loading properties and is suitably non-toxic for its intended use.

The organocatalyst can be an organic acid. Exemplary organic acids include diphenylphosphate, sulfuric acid, p-toluenesulfonic acid, methanesulfonic acid, and trifluoromethane sulfonic acid (triflic acid).

The organocatalyst can be a nitrogen base. The nitrogen base can also serve as an accelerator for another ROP catalyst. Exemplary nitrogen base catalysts include triallylamine, triethylamine, tri-n-octylamine and benzyldimethylamine. Other nitrogen base catalysts, shown in List 5 below, include pyridine (Py), N,N-dimethylaminocyclohexane (Me$_2$NCy), 4-N,N-dimethylaminopyridine (DMAP), trans-1,2-bis(dimethylamino)cyclohexane (TM-CHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof.

List 5

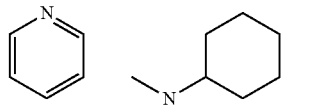

Pyridine (Py)  N,N-Dimethylaminocyclohexane (Me2NCy)

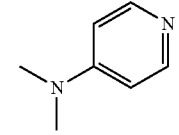
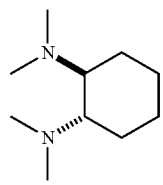

4-N,N-Dimethylaminopyridine (DMAP)     trans 1,2-Bis(dimethylamino)cyclohexane (TMCHD)

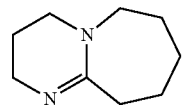
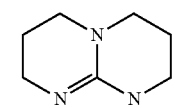

1,8-Diazabicyclo[5.4.0]undec-7-ene (DBU)     7-Methyl-1,5,7-triazabicyclo[4.4.0]dec-5-ene (MTBD)

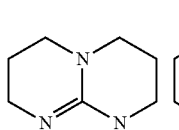
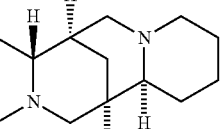

1,5,7-Triazabicyclo[4.4.0]dec-5-ene (TBD)     (-)Sparteine (Sp)

(Im-1)

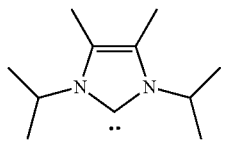

1,3-Bis(2-propyl)-4,5-dimethylimidazol-2-ylidene (Im-2)

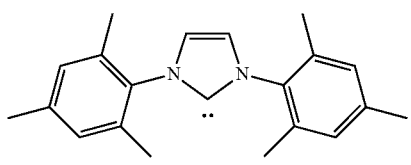

1,3-Bis(2,4,6-trimethylphenyl)imidazol-2-ylidene (Im-3)

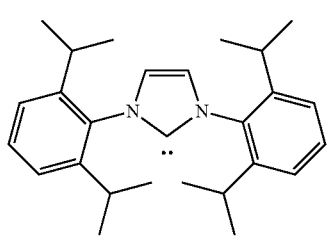

1,3-Bis(2,6-di-i-propylphenyl(imidazol-2-ylidene (Im-4)

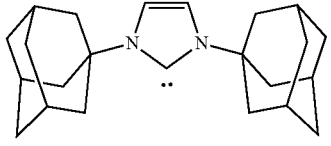

1,3-Bis(1-adamantyl)imidazol-2-yliden)

(Im-5)

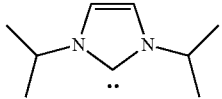

1,3-Di-i-propylimidazol-2-ylidene (Im-6)

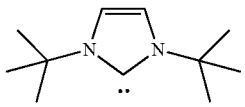

1,3-Di-t-butylimidazol-2-ylidene (Im-7)

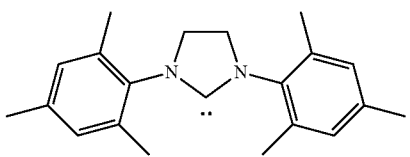

1,3-Bis(2,4,6-trimethylphenyl)-4,5-dihydroimidazol-2-ylidene (Im-8)

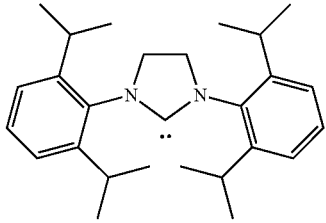

1,3-Bis(2,6-di-i-propylphenyl)-4,5-dihydroimidazol-2-ylidene

A more specific organocatalyst is N-bis(3,5-trifluoromethyl)phenyl-N'-cyclohexylthiourea (TU):

(TU)

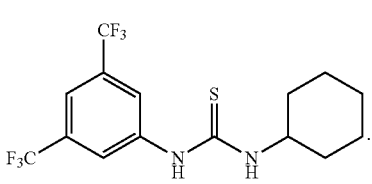

Other organocatalysts comprise at least one 1,1,1,3,3,3-hexafluoropropan-2-ol-2-yl (HFP) group. Singly-donating hydrogen bond catalysts have the formula (C-1):

$$R^2—C(CF_3)_2OH \quad (C\text{-}1),$$

wherein $R^2$ represents a hydrogen (H—*) or a monovalent group having 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are shown below.

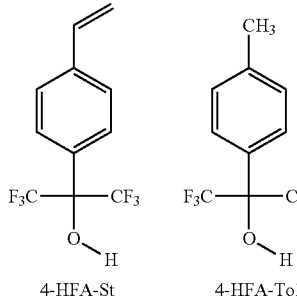 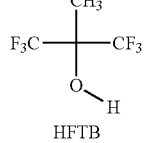

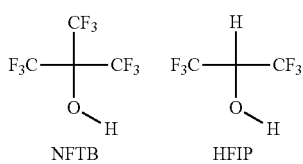

Other ROP organocatalysts include doubly-donating hydrogen bonding catalysts having two HFP groups, represented by the formula (C-2):

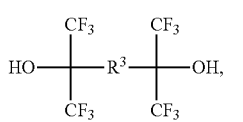

wherein R³ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, or a combination thereof. Representative double hydrogen bonding catalysts of formula (C-2) include those listed below. In a specific embodiment, R³ is an arylene or substituted arylene group, and the HFP groups occupy positions meta to each other on the aromatic ring.

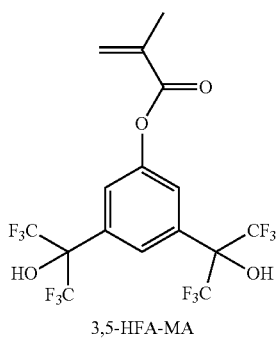

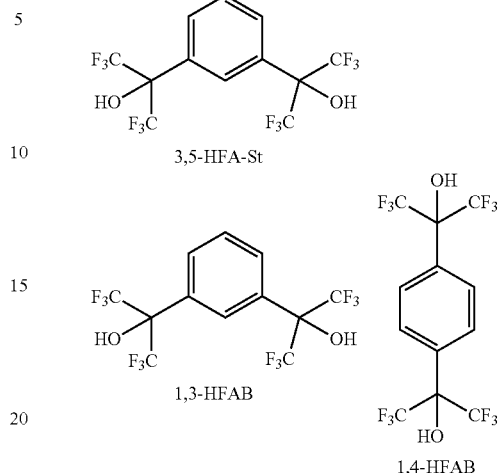

The HFP-containing groups can be covalently bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof.

The catalyst comprising charged HFP-containing groups can be bound by ionic association to oppositely charged sites on a polymer or a support surface.

The nitrogen base can be used alone as a catalyst when producing linear polymers by ring opening polymerization, such as the polymer arm precursor. Alternatively, the nitrogen bases can serve as an optional accelerator when used in combination with a primary catalyst, such as TU, in a ring opening polymerization. When employed as an accelerator, each nitrogen is potentially capable of participating as a Lewis base. In general, stronger nitrogen base accelerators improve the polymerization rate.

The ROP reaction mixture comprises at least one organocatalyst and, when appropriate, several organocatalysts together. The ROP catalyst can be added in a proportion of 1/20 to 1/40,000 moles relative to the cyclic carbonyl monomers, and preferably in a proportion of 1/1,000 to 1/20,000 moles relative to the cyclic carbonyl monomers.

Exceptions to the above have been found when attempting to generate the crosslinked core by ring opening polymerization using base catalysis alone. In these instances, nitrogen bases comprising 1 or 2 nitrogens have not generally been effective in forming unimolecular star polymers. The 1-nitrogen and 2-nitrogen base catalysts produced star polymers having high polydispersities (greater than 1.35), or products that were amorphous. After considerable experimentation, it was found that the formation of the crosslinked core by ring opening polymerization of a multi-functional cyclic ester monomer could be accomplished using a nitrogen base comprising three or more nitrogens. Unimolecular nano-sized amphiphilic star polymers having a polydispersity of 1.35 or less were successfully produced using this type of catalyst. One such base catalyst is 1,5,7-triazabicyclo [4.4.0]dec-5-ene (TBD). The examples further below demonstrate formation of a star polymer using TBD as the sole catalyst.

ROP Conditions

The ring-opening polymerization can be performed at a temperature of about 15° C. to 150° C., more preferably 20° C. to 80° C. Reaction times vary with solvent, temperature, agitation rate, pressure, and equipment. In general, the polymerizations are complete within 1 to 100 hours.

The ROP reaction is preferably performed with a solvent. Exemplary solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerizations are conducted using a dry, inert atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

The catalyst and the accelerator can be the same material. For example, some ring opening polymerizations can be conducted using 1,5,7-triazabicyclo[4.4.0]dec-5-ene (TBD) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer(s) used.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer used for the ROP.

The initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer(s).

The catalysts can be removed by selective precipitation or in the case of the solid supported catalysts, simply by filtration. The radical polymer can comprise residual catalyst in an amount greater than or equal to 0 wt % (weight percent), based on total weight of the radical polymer and the residual catalyst.

Average Molecular Weight

The core preferably has a number average molecular weight Mn of about 10,000 or more, more preferably about 20,000 to about 40,000, and most preferably about 25,000 to about 35,000.

Endcap Agents

Optionally, the crosslinked core can further be treated with an endcap agent to prevent further chain growth and stabilize the reactive end groups against unwanted side reactions such as chain scission. Endcap agents include, for example, materials for converting terminal hydroxyl groups to esters, such as carboxylic acid anhydrides and carboxylic acid chlorides. The endcap agent can also comprise a biologically active moiety, which becomes bound to the terminal end group of the ring opened polymer chain.

In an embodiment, the core comprises a living end group (i.e., is not end-capped), and is capable of initiating a ring opening polymerization.

In aqueous solution the mikto-arm star polymers disperse to form nano-sized particles having an average particle size of from 2 nm to 500 nm, 10 nm to 250 nm, and more particularly 50 nm to 200 nm, 50 nm to 150 nm, 50 nm to 120 nm, and even more particularly from 50 nm to 100 nm, as measured by dynamic light scattering. The particles can comprise one or more macromolecules of the mikto-arm star polymer.

Loaded Mikto-Arm Star Polymers

Figure 2:
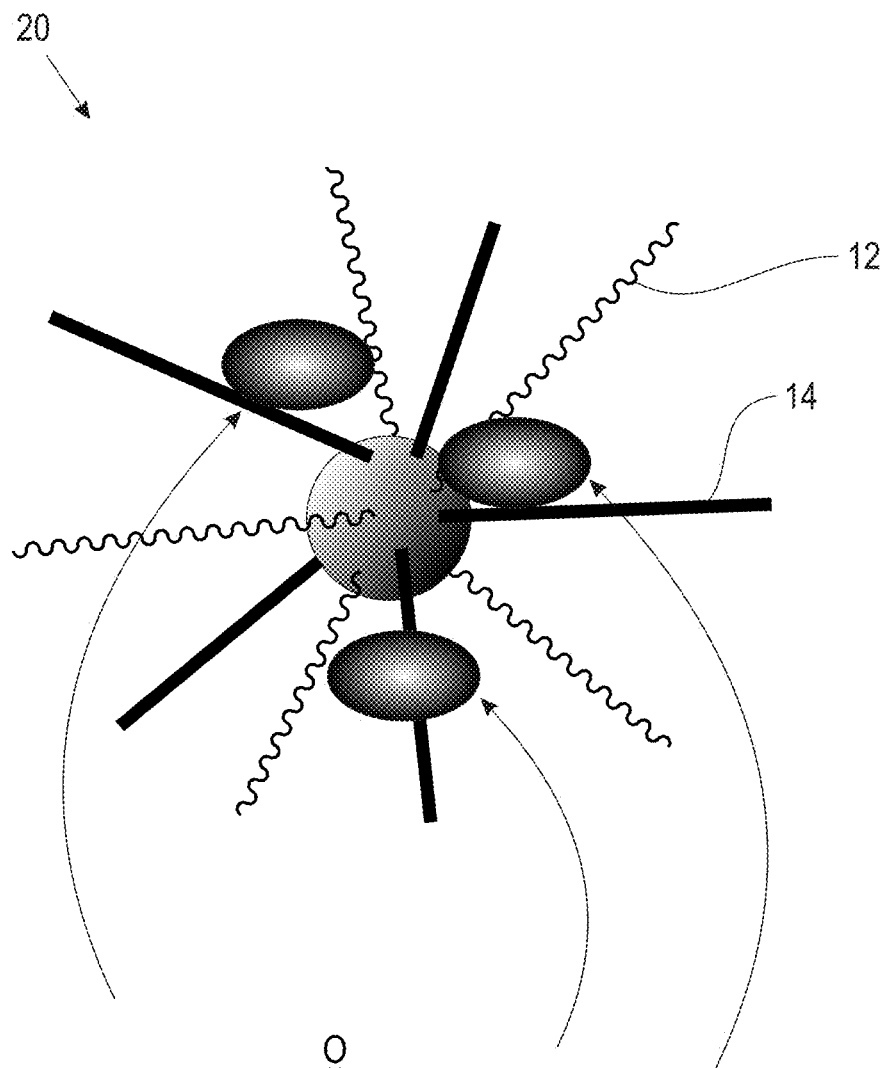
FIG. 2 is an illustration showing an exemplary non-limiting loaded mikto-arm star polymer, where 3 molecules of cargo, CoQ10, are occluded within the interstitial region of the polymer arms.
Figure 2:
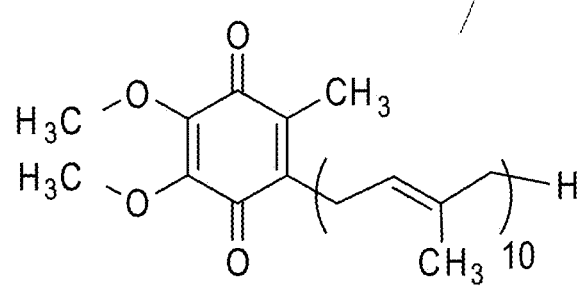

FIG. 2 is an illustration showing an exemplary non-limiting loaded mikto-arm star polymer 20, where 3 molecules of cargo compound, CoQ10, are occluded within the interstitial region of the polymer arms. In this example, the cargo and the star polymer are bound by non-covalent interactions.

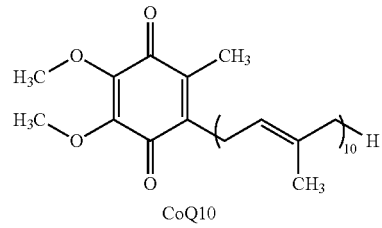

CoQ10

Cargo materials (therapeutic agents) can be used singularly or in combination. No limitation is placed on the cargo materials, with the proviso that the loaded mikto-arm star polymer can be dispersed in aqueous solution in the form of nano-sized particles, and the loaded mikto-arm star polymer performs a useful therapeutic function. Cargo materials include biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), vitamins (e.g., vitamin E compounds, vitamin D), dietary supplements including CoQ10 and ubiquinol, inorganic materials (e.g., metals and metal oxides), chromophores that aid in diagnostics (e.g., porphyrinoid compounds, including porphyrins and phthalocyanines), antimicrobial drugs, radioactive variants of the foregoing, and combinations of the foregoing. Some of the therapeutic agents can alter the chemical structure and/or activity of a cell, or can selectively alter the chemical structure and/or activity of a cell type relative to another cell type. As an example, one desirable change in a chemical structure can be the incorporation of a gene into the DNA of the cell. A desirable change in activity can be the expression of the transfected gene. Another change in cell activity can be the induced production of a desired hormone or enzyme. A desirable change in cell activity can also be the selective death of one cell type over another cell type. No limitation is placed on the relative change in cellular activity caused by the therapeutic agent, providing the change is desirable and useful. Other therapeutic agents herein improve diagnostic capability without necessarily altering the structure or activity of the tissue, organ, bone, or cell. These include image contrast enhancing agents for magnetic resonance imaging and x-ray imaging. The cargo material can comprise a metal, including one or more of the above-described restricted metals. The loaded mikto-arm star polymers can comprise therapeutic agents singularly or in combination.

Cargo materials can be bound covalently or non-covalently (e.g., by hydrophobic, hydrogen bonding, and/or electrostatic interactions) to the mikto-arm star polymer. The cargo material does not have to be released from the loaded mikto-arm star polymer in order to perform a useful therapeutic function. The cargo material can perform a useful therapeutic function while bound to the mikto-arm star polymer or after release from the star polymer.

The loaded mikto-arm star polymer can be administered as a powder, pill, paste, lotion, gel, or aqueous mixture using any suitable technique, including but not limited to liquid injections, solid or liquid ingestion, vapor inhalers, spray-on liquids, topically applied lotions, transdermal patches, solid and gel suppositories, ophthalmic gels, and/or ophthalmic drops.

In aqueous solution at a pH of from 5.0 to 8.0, the loaded mikto-arm star polymers are nano-sized particles, which can have an average cross-sectional circular diameter of from 2 nm to 500 nm, 2 nm to 250 nm, 2 nm to 150 nm, 2 nm to 120 nm, and more particularly 10 nm to 120 nm, 20 nm to 120 nm, 30 nm to 120 nm, and even more particularly from 50 nm to 120 nm, as measured by dynamic light scattering. A loaded mikto-arm star polymer can comprise, for example, 0.1 to 15 wt %, more particularly 5 to 15 wt %, of the therapeutic agent based on total dry weight of the loaded mikto-arm star polymer.

The loaded mikto-arm star polymers can comprise both small molecular weight therapeutic agents having a molecular weight in a range from 100 daltons to about 1,000 daltons as well as larger macromolecular materials, such as peptide and protein drugs having a molecular weight in a range from about 1,000 daltons to about 100,000 daltons, and beyond.

Contrast enhancing agents that have been considered for nuclear magnetic resonance imaging include soluble salts of paramagnetic metal ions, paramagnetic chelates and metallic complexes, and nitroxide stable free radicals. Paramagnetic metals ions include: from the transition metals series: titanium ($Ti^{3+}$), iron ($Fe^{3+}$), vanadium ($V^{4+}$), cobalt ($Co^{3+}$), chromium ($Cr^{3+}$), nickel ($Ni^{2+}$), manganese ($Mn^{2+}$), and copper ($Cu^{2+}$); from the Lanthanide series: praseodymium ($Pr^{3+}$), gadolinium ($Gd^{3+}$), europium ($Eu^{3+}$), and dysprosium ($Dy^{3+}$); from the Actinide series: protactinium ($Pa^{4+}$); and from nitroxide stable free radicals: pyrrolidine derivatives, and piperidine derivatives. Of these, the most favored contrast enhancing agents include complexes of ferric, chromium, and gadolinium ions, and stable nitroxide free radicals. Exemplary contrast enhancing agents for x-ray imaging include barium salts and halogenated materials, more particularly brominated and/or iodinated materials.

Organic contrast enhancing agents include porphyrinoids, which include but are not limited to porphyrins, corrins, chlorins, bacteriochlorophylls, phthalocyanines, tetraazaphyrins, texaphyrins, saphyrins, and the like. A non-limiting example of a porphyrinoid compound is 5,10,15,20-(3,5-ditertbutylphenyl)porphyrin, where the ligand M can be a metal or two hydrogens (M=2H) (DTBP):

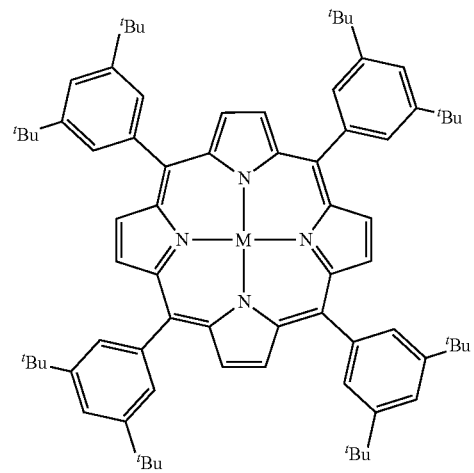

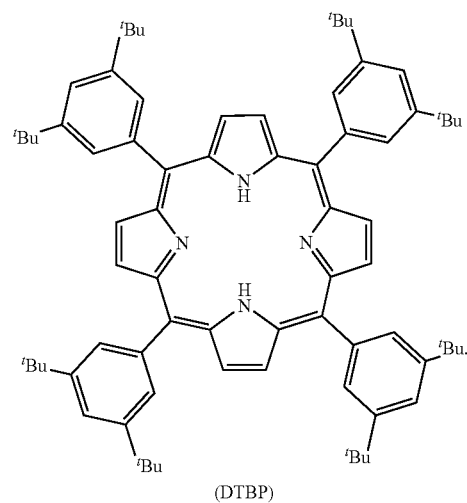

(DTBP)

Another non-limiting example of a porphyrinoid compound is tert-butyl phthalocyanine, wherein the ligand M can be a metal or two hydrogens (M=2H) (TBP):

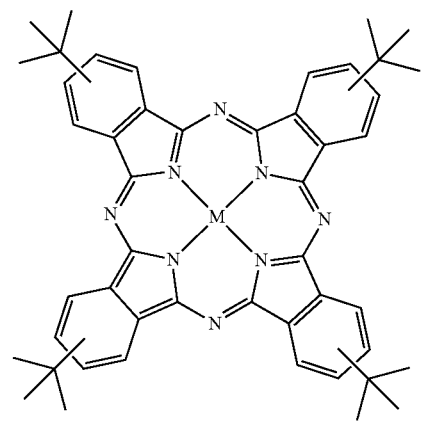

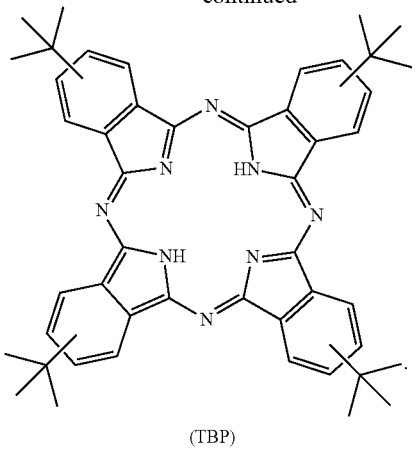

(TBP)

The contrast enhancing material can also comprise a combination of a porphyrinoid compounds. The porphyrinoid compound can further comprise a metal ligand that is a restricted metal.

The porphyrinoid compound can be in a non-aggregated state in the loaded mikto-arm star polymer, detectable by the fluorescence of an aqueous mixture of the loaded star polymer. In an embodiment, 10% to 100% by weight of the porphyrinoid compound in the loaded mikto-arm star polymer is in a non-aggregated state. In another embodiment, 50% to 100% by weight of the porphyrinoid compound in the loaded mikto-arm star polymer is in a non-aggregated state.

Exemplary protein drugs include peptide hormones such as insulin, glucagon, parathyroid hormone, calcitonin, vasopressin, renin, prolactin, growth hormone, the gonadotropins including chorionic gonadotropin, follicle stimulating hormone, thyroid stimulating hormone and luteinizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, platelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other non-limiting commercially available drugs used in medical treatments (e.g., cancers, microbial infections) include the following compounds, where the generic drug is enclosed in parentheses: 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRYLIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C(Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN® (Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), COSMOGEN® (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Prednisone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX® (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD® (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, *Erwinia* L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), FEMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte—Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin-2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL® (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MYLERAN® (Busulfan), MYLOCEL® (Hydroxyurea), MYLOTARG® (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Prednisone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Predni sone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (Vinblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, Vinorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

In an embodiment, the cargo is selected from the group consisting of ubiquinone (CoQ10), ubiquinol, and combinations thereof.

Also disclosed is a method of preparing a loaded mikto-arm star polymer, comprising i) forming a mixture of an amphiphilic mikto-arm star polymer and a therapeutic agent in a first solvent; and ii) combining the mixture with a second solvent, the second solvent being a non-solvent for the therapeutic agent, thereby forming nanoparticles of a loaded mikto-arm star polymer.

Also disclosed is an aqueous mixture comprising i) an above-described mikto-arm star polymer and ii) a therapeutic agent in contact with the core and/or with the polymer arms. In an embodiment, the therapeutic agent is selected from the group consisting of CoQ10, ubiquinol, and combinations thereof. In another embodiment the therapeutic agent is an image contrast enhancing material. In another embodiment, the contrast enhancing material is a porphyrinoid compound. In another embodiment, the contrast enhancing material is selected from the group consisting of

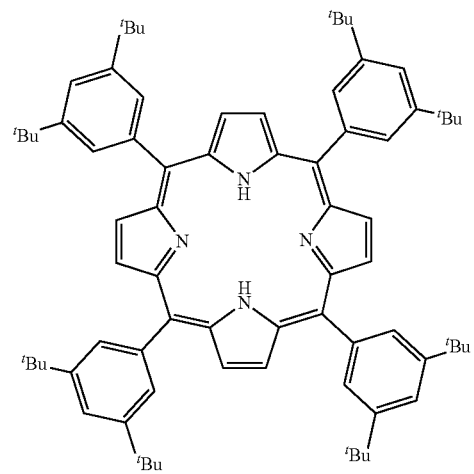

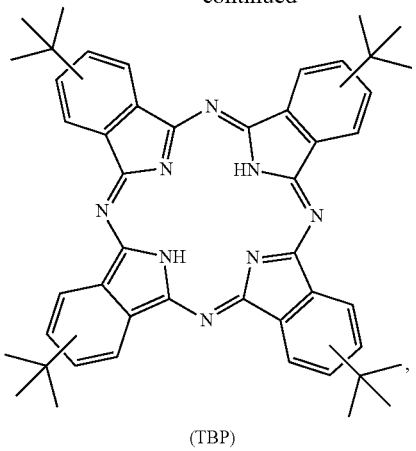

(TBP)

and combinations thereof.

In another embodiment, 10% to 100% of the image enhancing material is not aggregated in the loaded mikto-arm star polymer. In another embodiment, 50% to 100% of the image enhancing material is not aggregated in the loaded mikto-arm star polymer.

Further disclosed is a method of treating a cell, comprising contacting the cell with an aqueous mixture comprising the above described loaded mikto-arm star polymer. The biologically active cargo can comprise a single therapeutic agent or a mixture of therapeutic agents. The therapeutic agent can be a substance selected from the group consisting of dietary supplements, nutraceuticals, chemotherapy agents, antimicrobial agents, genes, dyes, image contrast enhancing materials, and combinations thereof. The therapeutic agent is a drug for treatment of cancer, for example doxorubicin. In an embodiment, the biologically active material is a porphyrinoid compound. Cells can be contacted in vitro, ex vivo, or in vivo. Contacting the cell induces 0% to 20%, 0% to 15%, 0% to 10%, 0% to 5%, 0% to 2%, or more particularly 0% to 1% cytotoxicity. In an embodiment, contacting the cell induces no cytotoxicity.

No restriction is placed on the type of cell that can be treated with the above-described loaded nanoparticles. In particular, the cells can be eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded mikto-arm star polymers can be used as non-viral transfection vectors. The target gene is not limited to any particular type of target gene or nucleotide sequence. For example, the target gene can be a cellular gene, an endogenous gene, an oncogene, a transgene, or a viral gene including translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

The preparation and use of the mikto-arm star polymers and loaded mikto-arm star polymers is further illustrated by the following examples.

EXAMPLES

Materials used in the following examples are listed in Table 1.

TABLE 1

Purchased materials

| Abbreviation | Description | Supplier |
|---|---|---|
| MPEG-OH | Poly(ethylene glycol) monomethyl ether, Mn 5000, PDI 1.05 | Fluka |
| BPPG-OH | Poly(propylene glycol) monobutyl ether, Mn 1000, PDI 1.05 | Sigma-Aldrich |
|  | Phytol, as a mixture of isomers | Sigma-Aldrich |
| TBD | 1,5,7-Triazabicyclo[4.4.0]dec-5-ene | Sigma-Aldrich |
| BCH | 4,4'-Bicyclohexanone | TCI Japan |
| BA | Benzoic Acid | Sigma-Aldrich |
|  | Toluene Anhydrous | Sigma-Aldrich |
|  | Diethyl Ether | Sigma-Aldrich |
| DCM | Dichloromethane | Sigma-Aldrich |

Herein, Mn is the number average molecular weight, Mw is the weight average molecular weight, and MW is the molecular weight of one molecule.

Monomethyl poly(ethylene glycol) (MPEG-OH), having a number average molecular weight of 5000 g/mol, PDI=1.02) obtained from Fluka, was purified azeotropically and recrystallized from benzene and dried under vacuum for 24 hours prior of use. 1,5,7-Triazabicyclo[4.4.0]dec-5-ene (TBD) was purified by sublimation under vacuum. Phytol was purified azeotropically and dried under vacuum for 24 hours prior of use. Anhydrous toluene, benzoic acid (BA) and diethyl ether were used as received.

Methods of Analysis $^1$H NMR spectra were recorded on a Bruker Avance 2000 spectrometer operating at 400 MHz (proton) and were referenced to internal solvent (CDCl$_3$, $^1$H=7.26 ppm). All NMR spectra were recorded at room temperature using standard Bruker library pulse programs. All chemicals and solvents were purchased from Sigma-Aldrich Chemical Co (Milwaukee, Wis.) except where indicated, unless stated otherwise. Deuterated solvents were purchased from Cambridge Isotopes (Andover, Mass.) and used as received. Analytical gel permeation chromatography (GPC) was performed in tetrahydrofuran (THF) using Waters high resolution columns HR1, HR2 and HR4E (flow rates 1 mL/minute) and peaks detected using a Waters 996 diode array and a Waters 411 differential refractometer, calibrated using polystyrene standards to determine molecular weight and polydispersity index (PDI). Dynamic Light Scattering (LS) measurements yielded values for Mw and hydrodynamic radii ($R_H$) using the described GPC column set with a Wyatt DAWN EOS multi-angle light scattering detector.

Bis-ε-caprolactone (BOD) was prepared from 4, 4'-bicyclohexanone according to the procedure of Nijenhuis, A. J. et al., Polymer 1996, 37, 2783.

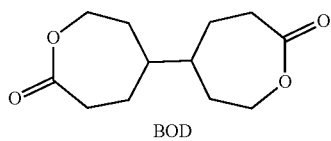

BOD give a white precipitate, which was then filtered and dried. The crude polymer was dissolved in dichloromethane (DCM, 7 mL), and diethyl ether (20 mL) was slowly added to a stirred solution. The resulting emulsion was allowed to settle for 5 hours, forming a transparent oil at the bottom of the flask. The solution was decanted off and the oil was dissolved in a minimum amount of DCM, precipitated from diethyl ether, filtered and dried under vacuum for 24 hours.

The mikto-arm star polymer has an average of x number of methyl ether terminated poly(ethylene oxide) arms (MPEO arms) and an average of y number of butyl ether terminated poly(propylene oxide) arms (BPPO arms), which are linked by respective terminal oxygens to a multivalent crosslinked polyester core formed by ring-opening polymerization of BOD (initiated by MPEG-OH and BPPG-OH). The MPEO arms have an average of m number of ethylene oxide units. The BPEO arms have an average of n number of propylene oxide units. The core has an average of q number of ester units derived from BOD. The core is a living core having z number of chain terminating hydrogen end groups. The valency of the core equals x+y+z.

The chemical structure of the mikto-star polymer is represented by the formula below.

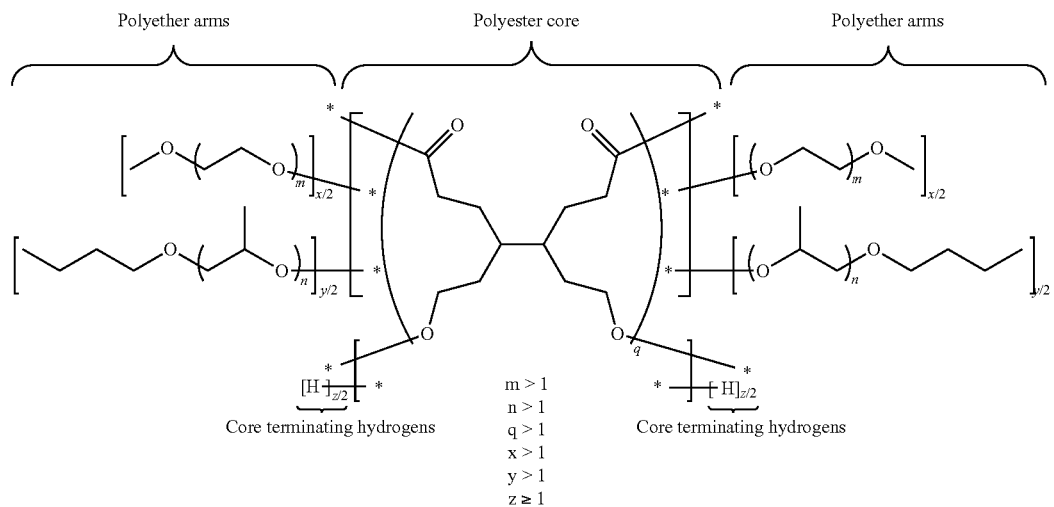

Phytol, as a mixture of isomers, has the structure.

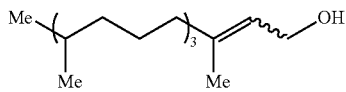

General procedure A for the synthesis of mikto-star polymer with mixed polyether arms.

In a glove box, to a solution of poly(ethylene glycol) monomethyl ether (MPEG-OH) of appropriate concentration in anhydrous toluene (5.5 mL), a corresponding amount of poly(propylene glycol) monobutyl ether (BPPG-OH) was added followed by the addition of bis-ε-caprolactone (BOD) (0.19 g, 0.84 mmol). Then, TBD solution (0.1 g, 5 wt % in toluene) was added to the reaction mixture. The resulting solution was allowed to stir at room temperature (RT) for 16 hours. The reaction was quenched with benzoic acid (10 mg) and the mixture was filtered through a 1 micrometer glass filter. Diethyl ether (30 mL) was added to the clear filtrate to In the examples that follow, RI refers to refractive index detector. LS refers to light scattering detector.

Example 1 (Comparative)

Star polymer with 0% BPPO arms (SP-1). SP-1 was synthesized according to general procedure A using MPEG-OH (0.550 g, 0.11 mmol) and no BPPG-OH. Star polymer SP-1 was a white amorphous polymer, (0.29 g, 53%). $^1$H NMR (CDCl$_3$, 400 MHz): δ (ppm)=4.9-3.9 (br, 32H, —CH$_2$—CH$_2$—OOC—), 3.58 (br, 386H, —O—CH$_2$—CH$_2$—O—, from the core —CH$_2$—OH), 3.30 (s, 3H, CH$_3$—O—CH$_2$), 2.9-2.1 (br, 3OH, —CH$_2$—CH$_2$—COO—), 1.9-1.4 (br, 52H, —OOC—CH$_2$—CH$_2$—CH$_2$—CH$_2$—OOC—). GPC (RI): Mn=109.1 kDa, PDI=1.1 $R_H$ (THF)=4.7 nm, Mw(LS, THF)=120 kDa; average number of arms=24 (x=24, y=0).

Example 2

Star Polymer with 10% BPPO arms (SP-2). SP-2 was synthesized according to general procedure A using MPEG-OH (0.495 g, 0.099 mmol) and BPPG-OH (0.011 g, 0.011 mmol). Star polymer SP-2 was a white amorphous powder. Yield: 0.28 g, 40%. $^1$H NMR: (CDCl$_3$, 400 MHz): δ (ppm)=4.4-3.85 (br., m. 11H), 3.84-3.43 (m, 5044H, —O—CH$_2$—CH$_2$—O— (MPEO)), 3.38 (s, 34H —OCH$_3$ (MPEO)), 1.17-1.11 (m, 48H, —O—CH$_2$—CH(CH$_3$)—O (BPPO); GPC (RI): Mn=108.2 kDa; PDI=1.1, R$_H$ (THF)=4.6 nm, Mw (LS, THF)=119.1 kDa. Average number of arms=26 (x=23.4, y=2.6).

Example 3

Star Polymer with 25% BPPO arms (SP-3). SP-3 was synthesized according to general procedure A using MPEG-OH (0.412 g, 0.0825 mmol) and BPPG-OH (0.028 g, 0.0275 mmol). SP-3 was a white amorphous powder (0.33 g, 37%). $^1$H NMR: (CDCl$_3$, 400 MHz): δ (ppm)=3.85-3.42 (m, 2098H, —O—CH$_2$—CH$_2$—O— (PEO)), 3.38 (s, 16H —OCH$_3$(PEO)), 1.17-1.11 (m, 48H, —O—CH$_2$—CH (CH$_3$)—O (PPO); GPC (RI): Mn=106.7 kDa; PDI=1.2; R$_H$ (THF)=4.6 nm, Mw (LS, THF)=128 kDa. Average number of arms=32 (x=24, y=8).

Example 4

Star Polymer with 50% BPPO arms (SP-4). SP-4 was synthesized according to general procedure A using MPEG-OH (0.275 g, 0.055 mmol) and BPPG-OH (0.055 g, 0.055 mmol). SP-4 was a white amorphous powder (0.36 g, 69%). $^1$H NMR (CDCl$_3$, 400 MHz): δ (ppm)=3.84-3.43 (m, 1279H, —O—CH$_2$—CH$_2$—O— (MPEO)), 3.38 (s, 8H —OCH$_3$ (MPEO)), 1.17-1.11 (m, 48H, —O—CH$_2$—CH (CH$_3$)—O (BPPO); GPC (RI): Mn=106.7 kDa, PDI=1.3; R$_H$ (THF)=4.7 nm, Mw (LS, THF)=140 kDa. Average number of arms=47 (x=23.5, y=23.5).

Example 5

Star Polymer with 75% BPPO arms (SP-5). SP-5 was synthesized according to general procedure A using MPEG-OH (0.137 g, 0.0275 mmol) and BPPG-OH (0.0825 g, 0.0825 mmol). SP-5 was a white amorphous powder (0.22 g, 53%). $^1$H NMR (CDCl$_3$, 400 MHz): δ (ppm)=3.84-3.43 (m, 895H, —O—CH$_2$—CH$_2$—O— (MPEO)), 3.38 (s, 5H —OCH$_3$(MPEO)), 1.17-1.11 (m, 48H, —O—CH$_2$—CH (CH$_3$)—O (BPPO); GPC (RI): Mn=107.5 kDa, PDI=1.2; R$_H$ (THF)=4.7 nm, Mw (LS, THF)=129 kDa. Average number of arms=65 (x=16.25, y=48.75).

General Procedure B for the Synthesis of Star Polymer with MPEO and Phytol Arms In a glove box, to a solution of MPEG-OH of appropriate concentration in anhydrous toluene (5.5 mL), a desired amount of phytol was added, followed by the addition of bis-ε-caprolactone (BOD) (0.19 g, 0.84 mmol). Then, TBD solution (0.1 g, 5 wt % in toluene) was added to the reaction mixture. The resulting solution was allowed to stir at RT for 16 hours. The reaction was quenched with benzoic acid (10 mg) and the mixture was filtered through a 1 micrometer glass filter. Diethyl ether (30 mL) was added to the clear filtrate to give a white precipitate, which was then filtered and dried. The crude polymer was dissolved in DCM (7 mL) and diethyl ether (20 mL) was slowly added to a stirred solution. The emulsion was allowed to settle for 5 hours, forming transparent oil at the bottom of the flask. The solution was decanted off and the oil was dissolved in a minimum amount of DCM, precipitated from ethyl ether, filtered and dried under vacuum for 24 hours.

The mikto-arm star polymer has an average of x' number of methyl ether terminated poly(ethylene oxide) arms (MPEO arms) and an average of y' number of phytoxy arms (i.e., PHY arms), which are linked by respective terminal oxygens to a multivalent crosslinked polyester core formed by ring-opening polymerization of BOD (initiated by MPEG-OH and Phytol). The MPEO arms have an average of m' number of ethylene oxide units. The core has an average of q' number of ester units derived from BOD. The core is a living core having z' number of chain terminating hydrogen end groups. The valency of the core equals x'+y'+z'.

The chemical structure of the phytol-based mikto-star polymers is represented by the formula below.

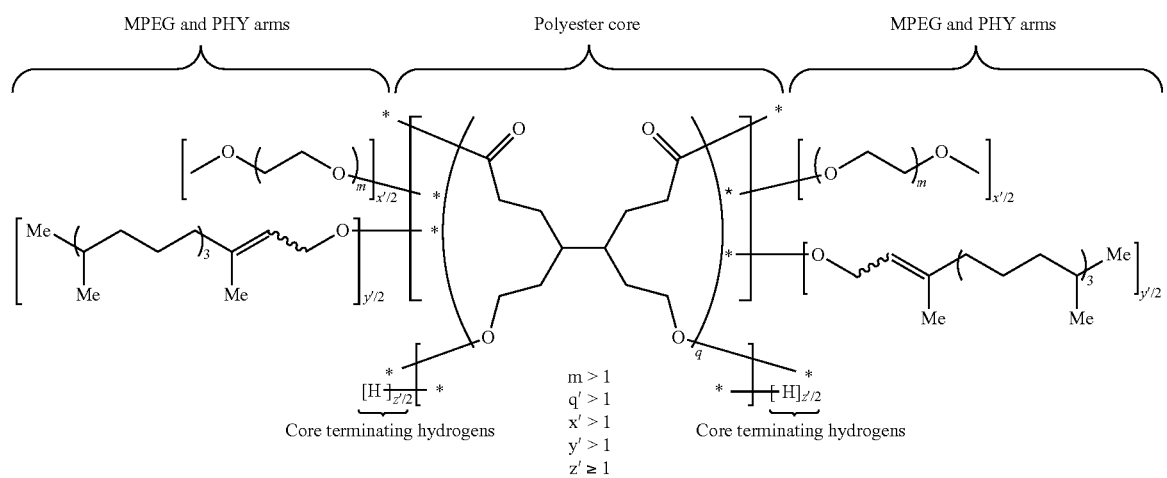

It should be understood that a given carbonyl group of the core can be linked to a divalent oxygen end group of an MPEG arm, a divalent oxygen end group of a PHY arm, or a divalent oxygen group of a different ring-opened BOD unit of the core. A given divalent oxygen of the core can be linked to a terminating hydrogen or a carbonyl group of a different ring-opened BOD unit of the core. A given MPEG arm can be linked to a carbonyl group of the core. A given PHY arm can be linked to a carbonyl group of the core. A given terminal hydrogen group can be linked to a divalent oxygen of the core, forming a terminal alcohol group of the core.

Example 6 (Comparative)

Example 6 is a repeat of Example 1, a star polymer with 0% Phytol arms (SP-6). SP-6 was synthesized according to general procedure B using MPEG-OH (0.550 g, 0.11 mmol) and no phytol. Star polymer SP-6 was a white amorphous powder, (0.29 g, 53%). $^1$H NMR (CDCl$_3$, 400 MHz): δ (ppm)=4.9-3.9 (br, 32H, —CH$_2$—CH$_2$—OOC—), 3.58 (br, 386H, —O—CH 2-CH 2-O—, from the core —CH$_2$—OH), 3.30 (s, 3H, CH$_3$—O—CH$_2$), 2.9-2.1 (br, 3OH, —CH$_2$—CH$_2$—COO—), 1.9-1.4 (br, 52H, —OOC—CH$_2$—CH$_2$—CH$_2$—CH$_2$—OOC—). GPC (RI): Mn=109.1 kDa, PDI=1.1 R$_H$ (THF)=4.7 nm, Mw(LS, THF)=120 kDa; average number of arms=24 (x'=24, y'=0).

Example 7

Star Polymer with 10% Phytol arms (SP-7). SP-7 was synthesized according to general procedure B using MPEG-OH (0.495 g, 0.099 mmol) and Phytol (0.00325 g, 0.011 mmol). SP-7 was a white amorphous powder. Yield: 0.27 g, 39%. $^1$H NMR (CDCl$_3$, 400 MHz): δ (ppm)=5.32 (br, s, phytol-C(CH$_3$)=CH—CH$_2$OH, 0.13H), 4.6-3.9 (br., m. 5H, —OCH$_2$CH$_2$CH(—CH))—CH$_2$CH$_2$CO— from the core and phytol group —C(CH$_3$)=CH—CH$_2$OH), 3.8-3.5 (br, s, 452H, —OCH$_2$CH$_2$O—), 3.4 (s, 3H —OCH$_3$), 2.9-2.2 (br, m, 0.14H, phytol group —C(CH$_3$)=CHCH$_2$OH), 2.2-1.8 (br, s, —OCH$_2$CH$_2$CH(—CH))—CH$_2$CH$_2$CO— from the core 1.25H), 1.8-1.0 (br, m, from phytol group CH$_3$(CH$_3$)CH(CH$_2$)$_3$CH(CH$_3$)(CH$_2$)$_3$CH(CH$_3$)—(CH$_2$)$_3$C(CH$_3$)=CHCH$_2$OH, 0.35H), 1.0-0.7 (br, d, CH$_3$(CH$_3$)CH(CH$_2$)$_3$CH(CH$_3$)(CH$_2$)$_3$CH—(CH$_3$)(CH$_2$)$_3$C(CH$_3$)=CHCH$_2$OH, 2H) GPC (RI): Mn=153.6 kDa, PDI=1.1; Rx (THF)=6 nm, Mw (LS, THF)=169.0 kDa; average number of arms=33.8 (x'=30.42, y'=3.38).

Example 8

Star Polymer with 25% Phytol arms (SP-8). SP-8 was synthesized according to general procedure B using MPEG-OH (0.412 g, 0.0825 mmol) and Phytol (0.008125 g, 0.0275 mmol). SP-8 was a white amorphous powder. Yield: 0.33 g, 49%. 41 NMR: (CDCl$_3$, 400 MHz): δ (ppm)=5.32 (br, s, phytol group —C(CH$_3$)=CH—CH$_2$OH, 0.28H), 4.6-3.9 (br, m, 7H, —OCH$_2$CH$_2$CH(—CH))—CH$_2$CH$_2$CO— from the core and phytol group —C(CH$_3$)=CH—CH$_2$OH), 3.8-3.5 (br, s, 452H, —OCH$_2$CH$_2$O—), 3.4 (s, 3H —OCH$_3$), 2.9-2.2 (br, m, 1.5H, phytol group —C(CH$_3$)=CHCH$_2$OH), 2.2-1.8 (br, s, —OCH$_2$CH$_2$CH(—CH))—CH$_2$CH$_2$CO— from the core 4H), 1.8-1.0 (br, m, from phytol group CH$_3$(CH$_3$)CH(CH$_2$)$_3$CH(CH$_3$)(CH$_2$)$_3$CH(CH$_3$)—(CH$_2$)$_3$C(CH$_3$)=CHCH$_2$OH, 7.2H), 1.0-0.7 (br, d, CH$_3$(CH$_3$)CH(CH$_2$)$_3$CH(CH$_3$)(CH$_2$)$_3$CH—(CH$_3$)(CH$_2$)$_3$C(CH$_3$)=CHCH$_2$OH, 4.3H) GPC (RI): Mn=140 kDa, PDI=1.1, R$_H$ (THF)=4.7 nm, Mw (LS, THF)=154.0 kDa; average number of arms=31 (x'=23.25, y'=7.75).

Example 9

Star Polymer with 50% Phytol arms (SP-9). SP-9 was synthesized according to general procedure B using MPEG-OH (0.275 g, 0.055 mmol) and Phytol (0.01625 g, 0.055 mmol). SP-9 was a white amorphous powder. Yield: 0.17 g, 59%. $^1$H NMR: (CDCl$_3$, 400 MHz): δ (ppm)=5.32 (br, s, 0.37H, phytol-C(CH$_3$)=CH—CH$_2$OH$_3$), 4.6-3.9 (br, m, 8H, —OCH$_2$CH$_2$CH(—CH))—CH$_2$CH$_2$CO— from the core and phytol group —C(CH$_3$)=CH—CH$_2$OH), 3.8-3.5 (br, s, 452H, —OCH$_2$CH$_2$O—), 3.4 (s, 3H —OCH$_3$), 2.9-2.2 (br, m, 7H, phytol group —C(CH$_3$)=CHCH$_2$OH), 2.2-1.8 (br, s, 67H —OCH$_2$CH$_2$CH(—CH))—CH$_2$CH$_2$CO— from the core), 1.8-1.0 (br, m, 5.36 from phytol group CH$_3$(CH$_3$)CH(CH$_2$)$_3$CH(CH$_3$)(CH$_2$)$_3$—CH(CH$_3$)(CH$_2$)$_3$C(CH$_3$)=CHCH$_2$OH), 1.0-0.7 (br, d, 2OH, CH$_3$(CH$_3$)CH(CH$_2$)$_3$CH—(CH$_3$)(CH$_2$)$_3$CH(CH$_3$)(CH$_2$)$_3$C(CH$_3$)=CHCH$_2$OH) GPC (RI): Mn=120 kDa; PDI=1.2, R$_H$ (THF)=6.3 nm, Mw (LS, THF)=144.0 kDa; average number of arms=29 (x'=14.5, y'=14.5).

Example 10

Attempted synthesis of star polymer with 75% Phytol arms (SP-10). SP-10 was synthesized according to general procedure B using MPEG-OH (0.137 g, 0.0275 mmol) and Phytol (0.024375 g, 0.0825 mmol). The preparation yielded no product.

Table 2 summarizes the preparations of the comparative (comp) and mikto-arm star polymers.

TABLE 2

| Example | Star Polymer Name | Cyclic Ester | Cyclic Ester (mg) | Cyclic Ester (mmol) | Initiator 1 | Initiator 1 (mg) | Initiator 1 (mmol)$^a$ | Initiator 2 | Initiator 2 (mg) | Initiator 2 (mmol)$^b$ | Initiator 2 (mol %)$^c$ |
|---|---|---|---|---|---|---|---|---|---|---|---|
| 1 (comp) | SP-1 | BOD | 190 | 0.837 | MPEG-OH | 550 | 0.11 | None | 0 | 0 | 0 |
| 2 | SP-2 | BOD | 190 | 0.837 | MPEG-OH | 495 | 0.099 | BPPG-OH | 11 | 0.011 | 10 |
| 3 | SP-3 | BOD | 190 | 0.837 | MPEG-OH | 412.5 | 0.0825 | BPPG-OH | 27.5 | 0.0275 | 25 |
| 4 | SP-4 | BOD | 190 | 0.837 | MPEG-OH | 275 | 0.055 | BPPG-OH | 55 | 0.055 | 50 |
| 5 | SP-5 | BOD | 190 | 0.837 | MPEG-OH | 137.5 | 0.0275 | BPPG-OH | 82.5 | 0.0825 | 75 |
| 6 (comp) | SP-6 | BOD | 190 | 0.837 | MPEG-OH | 550 | 0.11 | None | 0 | 0 | 0 |

TABLE 2-continued

| Example | Star Polymer Name | Cyclic Ester | Cyclic Ester (mg) | Cyclic Ester (mmol) | Initiator 1 | Initiator 1 (mg) | Initiator 1 (mmol)[a] | Initiator 2 | Initiator 2 (mg) | Initiator 2 (mmol)[b] | Initiator 2 (mol %)[c] |
|---|---|---|---|---|---|---|---|---|---|---|---|
| 7 | SP-7 | BOD | 190 | 0.837 | MPEG-OH | 495 | 0.099 | Phytol | 3.25 | 0.011 | 10 |
| 8 | SP-8 | BOD | 190 | 0.837 | MPEG-OH | 412.5 | 0.0825 | Phytol | 8.125 | 0.0275 | 25 |
| 9 | SP-9 | BOD | 190 | 0.837 | MPEG-OH | 275 | 0.055 | Phytol | 16.25 | 0.055 | 50 |
| 10 | SP-10 | BOD | 190 | 0.837 | MPEG-OH | 137.5 | 0.0275 | Phytol | 24.375 | 0.0825 | 75 |

[a]based on MPEG-OH Mn = 5000, PDI = 1.05
[b]based on Phytol MW = 296.5 and BPPG-OH Mn = 1000
[c]mmol initiator 2/mmol initiator 1 × 100%

Table 3 summarizes the properties of the comparative and mikto-arm star polymers. The term kDa means kiloDaltons.

TABLE 3

| Example | Star Polymer Name | Arm 1 | Arm 2 | Arm 2 (mol %)[a] | Mn (kDa) | Mw (kDa) | PDI | Rh (nm) |
|---|---|---|---|---|---|---|---|---|
| 1 (comp) | SP-1 | MPEG-OH | | 0 | 109.1 | 120 | 1.1 | 4.7 |
| 2 | SP-2 | MPEG-OH | BPPG-OH | 10 | 108.2 | 119 | 1.1 | 4.6 |
| 3 | SP-3 | MPEG-OH | BPPG-OH | 25 | 106.7 | 128 | 1.2 | 4.6 |
| 4 | SP-4 | MPEG-OH | BPPG-OH | 50 | 107.7 | 140 | 1.3 | 4.7 |
| 5 | SP-5 | MPEG-OH | BPPG-OH | 75 | 107.5 | 129 | 1.2 | 4.7 |
| 6 (comp) | SP-6 | MPEG-OH | | 0 | 109.1 | 120 | 1.1 | 4.7 |
| 7 | SP-7 | MPEG-OH | Phytol | 10 | 153.6 | 169 | 1.1 | 6.0 |
| 8 | SP-8 | MPEG-OH | Phytol | 25 | 140 | 154 | 1.1 | 4.7 |
| 9 | SP-9 | MPEG-OH | Phytol | 50 | 120 | 144 | 1.2 | 6.4 |
| 10 | SP-10 | MPEG-OH | Phytol | 75 | No product | | | |

[a]based on Phytol MW = 296.5, BPPG-OH Mn = 1000, and MPEG-OH Mn = 5000

General Procedure C for Preparation of Loaded Mikto-Arm Star Polymers

In a typical procedure, a loaded mikto-arm star polymer (having prefix LSP) was prepared according to the following procedure: Stock solutions of star polymer and CoQ10 were prepared separately in anhydrous THF and combined to form a solution containing star polymer (20 mg) and CoQ10 (2 mg, initially 10 wt % of the initial weight of the star polymer) in THF (0.2 mL). Water (4 mL) was rapidly added to the homogeneous solution while stirring. The resulting solution was sparged with $N_2$ approximately 3 hours to remove the organic solvent residue and was filtered through 0.4 micrometer Nylon filter. The filtered solution was analyzed by ultraviolet-visible light absorption (UV-Vis) to determine the drug loading (DL) as wt % drug based on the initial weight of star polymer and encapsulation efficiencies (EE) as % of initial drug loaded.

Table 4 summarizes the properties of the loaded star polymers. Comparative Examples 11 and 16 are duplicates.

TABLE 4

| Example | Loaded Star Polymer Name | Star Polymer Name | Arm 1 | Arm 2 | Arm 2 (mol %)[a] | Star Polymer (mg) | Cargo | Cargo Initial amount (mg) | Loaded CoQ10 (wt %)[b] | EE[c] |
|---|---|---|---|---|---|---|---|---|---|---|
| 11 (comp) | LSP-1 | SP-1 | MPEO | | 0 | 20 | CoQ10 | 2 | 3.2 | 31.2 |
| 12 | LSP-2 | SP-2 | MPEO | BPPO | 10 | 20 | CoQ10 | 2 | 9.9 | 97.0 |
| 13 | LSP-3 | SP-3 | MPEO | BPPO | 25 | 20 | CoQ10 | 2 | 8.7 | 85.0 |
| 14 | LSP-4 | SP-4 | MPEO | BPPO | 50 | 20 | CoQ10 | 2 | 9.5 | 91.6 |
| 15 | LSP-5 | SP-5 | MPEO | BPPO | 75 | 20 | CoQ10 | 2 | 7.1 | 68.6 |
| 16 (comp) | LSP-6 | SP-6 | MPEO | | 0 | 20 | CoQ10 | 2 | 3.2 | 31.2 |
| 17 | LSP-7 | SP-7 | MPEO | PHY | 10 | 20 | CoQ10 | 2 | 8.0 | 65.1 |
| 18 | LSP-8 | SP-8 | MPEO | PHY | 25 | 20 | CoQ10 | 2 | 8.6 | 76.0 |
| 19 | LSP-9 | SP-9 | MPEO | PHY | 50 | 20 | CoQ10 | 2 | 8.7 | 77.9 |

[a]based on Phytol MW = 296.5; based on BPPG-OH Mn = 1000
[b]based on total weight of the loaded star polymer
[c]Percent of initial amount of cargo loaded into the star polymer The results of Table 4 show that significantly higher loading levels (wt % of CoQ10) are obtained when Arm 2 (BPPO or PHY) was present in amounts greater than 0 mol %. At 10-50 mol % Arm 2, higher CoQ10 loading levels were obtained with BPPO arms (8.7-9.9 wt %) compared to PHY arms (8.0-8.7 wt %), although loading levels in each case were 2.2 times or more above the loading level of comparative examples 11 and 16 (3.2 wt % CoQ10, 0 mol % Arm 2). The highest CoQ10 loading level was obtained with 10 mol % BPPO (9.9 wt % CoQ10). The effective mol % range of BPPO arms was greater than 0 mol % and up to about 75 mol %. The effective mol % range of PHY arms was greater than 0 mol % and up to about 50 mol %. The results are promising for medical applications requiring the delivery and release of CoQ10 using biocompatible and/or biodegradable vehicles.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A mikto-arm star polymer, comprising:
   a crosslinked hydrophobic polymer core C', wherein C' comprises a polymer backbone selected from the group consisting of polyester, polycarbonate, and polyestercarbonate;
   a hydrophilic first arm covalently linked to core C', the first arm comprising a poly(ethylene oxide) chain, designated PEG chain; and
   a hydrophobic second arm covalently linked to the core, the second arm comprising a poly(propylene oxide) chain, designated PPG chain, or a phytoxy group.

2. The mikto-arm star polymer of claim 1, wherein the second arm comprises a PPG chain.

3. The mikto-arm star polymer of claim 1, wherein the second arm comprises a phytoxy group.

4. A composition, comprising:
   the mikto-arm star polymer of claim 1;
   a therapeutic agent used in a treatment of cellular tissue;
   wherein
   the therapeutic agent and mikto-arm star polymer are bound by non-covalent interactions.

5. The composition of claim 4, wherein the treatment is a medical treatment for a wound and/or a disease.

6. The composition of claim 4, wherein the treatment is a cosmetic treatment.

7. The composition of claim 4, wherein the composition is used as a dietary supplement.

8. The composition of claim 4, wherein the therapeutic agent is an antimicrobial agent.

9. The composition of claim 4, wherein the therapeutic agent is a nutraceutical for a medical treatment.

10. The composition of claim 9, wherein the nutraceutical is ubiquinone and/or ubiquinol.

11. A method of forming the composition of claim 4, comprising i) forming a mixture of the mikto-arm star polymer and a therapeutic agent in a first solvent; and ii) combining the mixture with a second solvent, the second solvent being a non-solvent for the therapeutic agent, thereby forming the composition.

12. The method of claim 11, wherein the second solvent is water.

13. A method of a treating a cell, comprising contacting the cell with an aqueous mixture comprising the composition of claim 4.

14. A mikto-arm star polymer of formula (2):

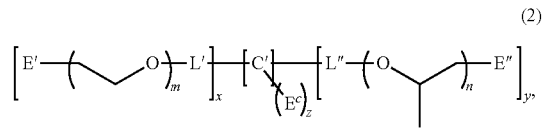

(2)

wherein
   x is a positive number having a value of 1 or more,
   y is a positive number having a value of 1 or more,
   z is a positive number having a value of 1 or more,
   m is a positive number having an average value of 50 to 600,
   n is a positive number having an average value of 10 to 50,
   x+y has a value of 6 or more,
   C' is a crosslinked polymer core having a valency of x+y+z, and C' comprises a polymer backbone selected from the group consisting of polyester, polycarbonate, and polyestercarbonate,
   each $E^c$ is an independent monovalent end group of the core C',
   each E' is an independent monovalent end group,
   each E" is an independent monovalent end group,
   each L' is an independent group selected from the group consisting of single bond and divalent linking groups, and
   each L" is an independent group selected from the group consisting of single bond and divalent linking groups.

15. The mikto-arm star polymer of claim 14, wherein C' is a crosslinked polyester core.

16. The mikto-arm star polymer of claim 14, wherein $E^c$ is hydrogen.

17. The mikto-arm star polymer of claim 14, wherein L' is a single bond.

18. A mikto-arm star polymer of formula (3):

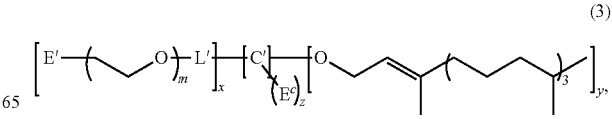

(3)

wherein
- x is a positive number having a value of 1 or more,
- y is a positive number having a value of 1 or more,
- z is a positive number having a value of 1 or more,
- m is a positive number having an average value of 50 to 600,
- x+y has a value of 6 or more,
- C' is a crosslinked polymer core having a valency of x+y+z, and C' comprising a polymer backbone selected from the group consisting of polyester, polycarbonate, and polyestercarbonate,
- each $E^c$ is an independent monovalent end group of the core C',
- each E' is an independent monovalent end group, and
- each L' is an independent group selected from the group consisting of single bond and divalent linking groups.

19. The mikto-arm star polymer of claim 18, wherein C' is a crosslinked polyester core.

20. The mikto-arm star polymer of claim 18, wherein $E^c$ is hydrogen.

21. The mikto-arm star polymer of claim 18, wherein L' is a single bond.

\* \* \* \* \*